US008843416B2

(12) United States Patent
Scelzi et al.

(10) Patent No.: US 8,843,416 B2
(45) Date of Patent: Sep. 23, 2014

(54) DETERMINING ENERGY CONSUMPTION IN A STRUCTURE

(75) Inventors: Michael Craig Scelzi, Glen Allen, VA (US); William Shawn Bonwell, Montpelier, VA (US); Allan H. Vaitses, Marion, MA (US); Mark Christopher Hartman, Amelia, VA (US); James Scelzi, Paducah, KY (US)

(73) Assignee: Netesco LLC, Richmond, VA (US)

( * ) Notice: Subject to any disclaimer, the term of this patent is extended or adjusted under 35 U.S.C. 154(b) by 0 days.

(21) Appl. No.: 12/960,149

(22) Filed: Dec. 3, 2010

(65) Prior Publication Data

US 2012/0065789 A1 Mar. 15, 2012

Related U.S. Application Data

(63) Continuation-in-part of application No. 12/557,992, filed on Sep. 11, 2009, now abandoned.

(51) Int. Cl.
*G06Q 20/00* (2012.01)
*G06Q 20/14* (2012.01)

(52) U.S. Cl.
CPC .................................. *G06Q 20/145* (2013.01)
USPC ................ 705/63; 705/34; 700/286; 700/295

(58) Field of Classification Search
USPC ............................... 705/63, 34; 700/286, 295
See application file for complete search history.

(56) References Cited

U.S. PATENT DOCUMENTS

| | | | |
|---|---|---|---|
| 4,647,221 | A | 3/1987 | Szabo |
| 6,622,097 | B2 | 9/2003 | Hunter |
| 6,657,552 | B2 | 12/2003 | Belski et al. |

(Continued)

FOREIGN PATENT DOCUMENTS

DE 102006049717 B3 4/2008

OTHER PUBLICATIONS

Nov. 15, 2013 Extended European Search Report issued in European Application No. 11191905.6.

(Continued)

*Primary Examiner* — Calvin L Hewitt, II
*Assistant Examiner* — John M Winter
(74) *Attorney, Agent, or Firm* — Banner & Witcoff, Ltd.

(57) ABSTRACT

Methods, apparatus, and systems are provided for measuring the supply of a consumable product/energy source, such as electrical power, to a facility over time and analyzing the measurements to determine the consumption or supply of the product by one or more loads and/or sources in the facility, and to determine induced and residual heat flow through the facility's envelope. Various aspects compare the measured supply of the consumable product to a database of consumption signatures, which characterize access to the consumable product by particular users. In doing so, costs for the product may be more accurately divided between different tenants of the facility without having to install individual services or measurement equipment for each individual tenant. Operating conditions and facility characteristics, such as temperatures, load factors, insulation factors, etc., may be further considered in determining a particular user's access of the consumable product. To aid in the controlling of energy use, thermal resistance factors of the building are determined, which are based on the induced and residual heat flow through the facility. Various algorithms are used including smart agents (e.g. neural networks) to determine the consumption of the consumable product by a particular user, to create the database of consumption signatures, and to determine the thermal resistance factors.

20 Claims, 14 Drawing Sheets

(56) References Cited

U.S. PATENT DOCUMENTS

| | | | |
|---|---|---|---|
| 6,819,098 | B2 | 11/2004 | Villicana et al. |
| 6,944,555 | B2 | 9/2005 | Blackett et al. |
| 7,373,221 | B2* | 5/2008 | Lal ............................... 700/291 |
| 8,186,873 | B1 | 5/2012 | Madding |
| 2002/0134541 | A1 | 9/2002 | Nelson |
| 2003/0016730 | A1 | 1/2003 | Daily et al. |
| 2003/0171851 | A1 | 9/2003 | Brickfield et al. |
| 2003/0225483 | A1 | 12/2003 | Santinato et al. |
| 2005/0154898 | A1* | 7/2005 | Chao ............................ 713/185 |
| 2006/0209857 | A1 | 9/2006 | Hicks, III |
| 2007/0006329 | A1* | 1/2007 | Morrow et al. ................ 726/34 |
| 2007/0055640 | A1 | 3/2007 | Dababneh et al. |
| 2007/0235550 | A1 | 10/2007 | Donath et al. |
| 2008/0092644 | A1 | 4/2008 | Hasebe |
| 2008/0159616 | A1 | 7/2008 | Fellinger |
| 2009/0083167 | A1* | 3/2009 | Subbloie ........................ 705/34 |
| 2009/0319905 | A1* | 12/2009 | Loeb et al. .................... 715/736 |
| 2010/0211222 | A1 | 8/2010 | Ghosn |
| 2011/0004764 | A1* | 1/2011 | Stuber ........................... 713/176 |
| 2012/0065789 | A1 | 3/2012 | Scelzi et al. |

OTHER PUBLICATIONS

Zhu et al., Detalied energy saving performance analyses on thermal mass walls demonstrated in a zero energy house, Mar. 2009, Energy and Buildings, vol. 41, Issue 3, pp. 303-310.

Cabeza et al., Experimental study on the performance of insulation materials in Mediterranean construction, May 2010, Energy and Buildings, vol. 42, Issue 5, pp. 630-636.

* cited by examiner

DETERMINING ENERGY CONSUMPTION IN A STRUCTURE

This application is a continuation-in-part of copending U.S. patent application Ser. No. 12/557,992, entitled Determining Consumption and/or Generation of Consumable Products in a Distributed System, filed Sep. 11, 2009, herein incorporated herein by reference in its entirety.

FIELD OF THE DISCLOSURE

Aspects relate generally to measuring consumption and production of a consumable product in a distribution system by one or more loads and/or sources. Further aspects relate generally to measuring energy efficiency of buildings via direct measurements as opposed to calculated theoretical measurements and/or utilizing these direct measurements in incentive based construction contracts. Methods, apparatus, and systems are disclosed which determine access to the consumable product (e.g., electricity) by a particular load or source in the distribution system through the use of techniques which characterize consumption/generation of the consumable product by one or more of the loads or sources. The methods, apparatus, and systems further provide real time monitoring of environmental conditions and usage of a building to characterize the building's current and historical energy performance and/or R-value.

BACKGROUND

Utility costs represent one of the largest expenses effecting net operating cost of residential, commercial, and industrial facilities. For example, a large office building comprised of 60,000 square feet will have an electrical consumption of approximately $10,000 monthly in the Mid Atlantic states in the summer months. Knowing how a building is being utilized by its tenants and knowing the building energy performance are both factors in understanding and controlling these costs.

SUMMARY

With respect to building utilization, tenants are constantly connecting electrical consumption devices including servers and other electric equipment not only to dedicated tenant lines but also to building power lines. Being able to recover this cost from tenants of the facility is critical to maximizing value, maximizing loan capacity of the facility, and maximizing revenue stream generated from the facility. However, being able to accurately match the consumption of utilities such as electrical power to individual tenants and/or buildings is often difficult. Further, some tenants and/or buildings will provide for generation of power for input into a smart grid. These generation facilities may include, for example, solar panels and/or wind generation facilities located proximate to buildings such as on top of buildings. There is a need to account for these installations. Additionally, electrical power, which is distributed to a number of tenants, may be provided to a facility with one supply service measured by one meter. To recover the cost of the electrical power, the facility manager may have to install costly additional supply services and meters or retro-fit the electrical distribution system in the facility such that each tenants electrical usage can be measured individually. Alternatively, the cost of the utility may be averaged and allocated to each tenant equally.

Situations may arise where one tenant consumes a disproportionate amount of the utility. For example, a particular tenant may install high powered add-on equipment such as computer server rooms, laboratory systems, or cellular network towers. In such cases, the facility operator may find that averaging the utility cost across all of the tenants may push the facility's fixed cost per square-foot to be greater than the facility's value per square-foot.

Building systems lack a simple understandable method for tracking the utility consumption. Due to the inability to simply track the consumption, building automation systems are often removed from service, electrically jumpered out of the distribution system, adjusted to extend start and stop times beyond optimal settings, not adjusted to reflect changes in the hours of occupancy from the original lease schedule, etc., and thus, the facility consumes more energy due to inadequate controls and monitoring. One technique to monitor and control the consumption is, for example, a graphical user interface which may be variously configured. In exemplary embodiments, it may be configured to compare historical values (as for example adjusted for outside temperature) with current values. The graphical user interface may employ an appropriate algorithm and graphical representations showing deviations which likely indicate either a problem or new energy usage by a particular tenant.

Another factor in controlling energy costs is understanding the thermal performance of the building's envelope (i.e., structure). Improving energy efficiency in new construction and in the remodeling of existing structures has become a primary concern, which is driven by such factors as utility costs, public concern for the environment and human health, government regulation, corporate social responsibility, globalization, and other market forces. In response to this concern, industry groups have formed, which put forth efficiency guidelines and certification programs for builders to follow. These certifications and other design benchmarks require energy efficiency to be addressed early in the design and construction process.

These requirements and verifications typical are based on simulation of building models, and an as-built structure may not, and often does not, meet the energy performance requirements of the planned design on day-one after completion. The errors in the simulation may be caused by design variations that are not reflected in the model, construction of the structure which is not to specification, incorrect assumptions on building usage and weather, utility equipment which is not installed correctly or functioning according to specification, insufficient model fidelity, and numerous other factors. Further, a building's energy performance may change over time due to the aging of materials, modifications to building structures and systems, or damage to the structures and systems.

Currently, no means exist to comprehensively measure a building's actual energy performance or to monitor the energy performance over time. Thus, the verification and management of a building's designed energy efficiency is based on incomplete or inaccurate information.

To overcome these problems described above and other problems, methods and systems are needed to determine the use of a utility by individual tenants, and to provide comprehensive in-situ measurement of a building's actual energy performance. These techniques allow building developers to insert incentive provisions in their contracts to ensure that buildings actually meet their design requirements. The end result may be specified without micromanaging the building process. This allows the building process to proceed as efficiently as possible and allows new technologies to be easily integrated without renegotiating the overall contract.

This Summary is provided to introduce a selection of concepts in a simplified form that are further described below in the Detailed Description. This Summary is not intended to identify key features or essential features of the invention.

Various techniques are presented for measuring the supply of a consumable product, such as electrical power, to a facility over time and analyzing the measurements to determine the consumption or supply of the product by one or more loads and/or sources (i.e. users) in the facility. Various aspects compare the measured supply of the consumable product to a database of signatures, and/or lease schedules which characterize access to the consumable product by particular users. In one exemplary embodiment, the supply of consumable product to the HVAC system may be measured and analyzed as compared to the inside temperature, outside temperature, sun loading, and heat generated by other devices such as lighting and computers to determine the overall R-value of a building.

The various techniques may be used, for example, in facilities to provide detailed reports of the usage of utilities such as electrical power, gas, and water, by multiple different users connected to a common measurable supply of the product. In doing so, the various techniques may be used to more accurately divide the cost of such utilities between different tenants of the facility without having to install individual services that can be individually measured for each tenant. In addition, by analyzing real time data and historical utility signatures the user can modify schedules to match leases, verify equipment operation either on/off, and verify large equipment loads by reviewing building utility signatures.

In a first embodiment, measurements are made from a common service, recorded as a data sequence, and transmitted to one or more processors for analyses. The processor(s) may retrieve signatures from a database to analyze various parameters such as the data sequences and determine, for example, different parameters such as how much of the measured product is consumed or produced by one or more particular users within a group of users connected to the measured service. Reports may then be generated which detail the use and/or supply.

In other embodiments operating conditions of the various users in the facility are measured at the same time supply of the consumable product may be measured. These operating conditions may be stored and/or transmitted to the processor(s), and the processor(s) may be configured in various ways. In one configuration, the processors may use the operating conditions as additional data in determining the usage of the consumable product by one or more users. Operating conditions may include, for example, temperatures inside and outside of the facility, and/or the number of people in the facility. These parameters may be utilized to determine a base line and/or inform the building manager whenever the building varies from the baseline, potentially indicating an anomaly.

In another embodiment, artificial intelligence algorithms such as, for example, neural networks may be used in the analysis of the data sequences and/or signatures to determine the usage of one or more particular users. The artificial intelligence may develop and learn over time using both rule based input and learned input from a trained operator.

In other embodiments, the signatures may be created by monitoring the use and/or supply of the consumable product in the distribution system of a facility and comparing the monitored use and/or supply to measured or controlled operating conditions of users of the product within the facility. The signatures may be determined, for example, by training an artificial intelligence process such as a neural network with the measured supply and/or operating conditions.

Further techniques are presented for measuring induced and/or residual heat flow through a building envelope. Various illustrative induced heat flows include heat resulting from: electrical power flowing into a building and being converted to heat by the distribution system and by electrical loads; fuel such as natural gas flowing into the building to produce heat when used; water which flows into the building and carries heat by virtue of its thermal mass; climate control systems which mechanically move heat through the building; and people which dissipate heat while inside the building. Residual heat flow includes the passive heat transfer through the building structure which is induced by the difference in the environments within the building and outside of the building. These various induced and residual heat flows may be determined periodically and in real time.

In exemplary embodiments, the building may be qualified while minimizing the transient heat flows generated by people, water, and non-HVAC heat sources such as lights and computers. This qualification may take place both at initial building launch and after a set period of time such as after building buildout. Incentives may be built into the contract that are conditioned on meeting predetermined performance criteria, such as R-value criteria. These R-value criteria may be specified with and/or without transient heat flows minimized.

In various embodiments, the residual heat flow and thermal resistance of wall assemblies of the building are measured using embedded sensors within the wall and/or periodically using transportable sensors. In one embodiment, the sensors are embedded in the material making up a layer of the wall assembly by the manufacturer of that material layer. In another embodiment, a temperature probe is inserted through the layers of the wall, wherein the probe has the ability to sense multiple temperatures at incremental depths along the probe.

In further embodiments, a thermal resistance factor of the building envelope is determined based on the measured induced and/or residual heat flows. Thermal resistance factor, $R_C$, is often a composite measure of thermal performance of a building envelope. The thermal resistance factor may be determined statically, where some or all induced heat flow is cut off, and the inside and outside environments are monitored over time as they approach equilibrium with one another. In one aspect the thermal resistance factor is determined as the amount of time taken for equilibrium to be reached given predefined initial conditions. In another aspect, the thermal resistance factor is defined by the change in temperature over a given time period given at set of initial conditions.

In other embodiments, the thermal resistance factor may be determined dynamically, where induced heat flow and environmental conditions are periodically and/or continuously monitored in real time.

In various embodiments, the static or dynamic thermal resistance factors may be used in one or more additional processes. For example, in one embodiment, the process may utilize a one-time snapshot of thermal resistance factor and/or a thermal resistance factor determined repeatedly to capture changes in the thermal resistance factor over time. In embodiments, the method of determining a target thermal resistance factor and/or a required thermal resistance factor may be specified in a building contract as a design metric. In other embodiments, the specific methods for determining $R_C$ may be used as industry standards to compare different structures, or to establish minimum build criteria. In still other embodiments, the thermal resistance factor may be used along with measured or forecasted environment conditions in a closed loop system to control the climate control system of the building. For example, the closed loop system may further control the climate control system and/or other building systems based on utility usage by different users as determined above based on user signatures.

Other various embodiments include systems, equipment, processes, and computer readable memory storing machine executable instructions for performing the functions of the embodiments described above.

BRIEF DESCRIPTION OF THE DRAWINGS

A more complete understanding of the disclosure and the advantages thereof may be acquired by referring to the following description in consideration of the accompanying figures, in which like reference numerals in different figures indicate similar elements, in which the first portion of each reference numeral corresponds to the figure number in which the referenced element is first introduced, and wherein.

DETAILED DESCRIPTION

In the following description of the various embodiments, reference is made to the accompanying drawings, which form a part hereof, and which are shown by way of illustration. It is to be understood that other embodiments may be utilized and structural and functional modifications may be made without departing from the scope of the disclosure.

Figure 1:
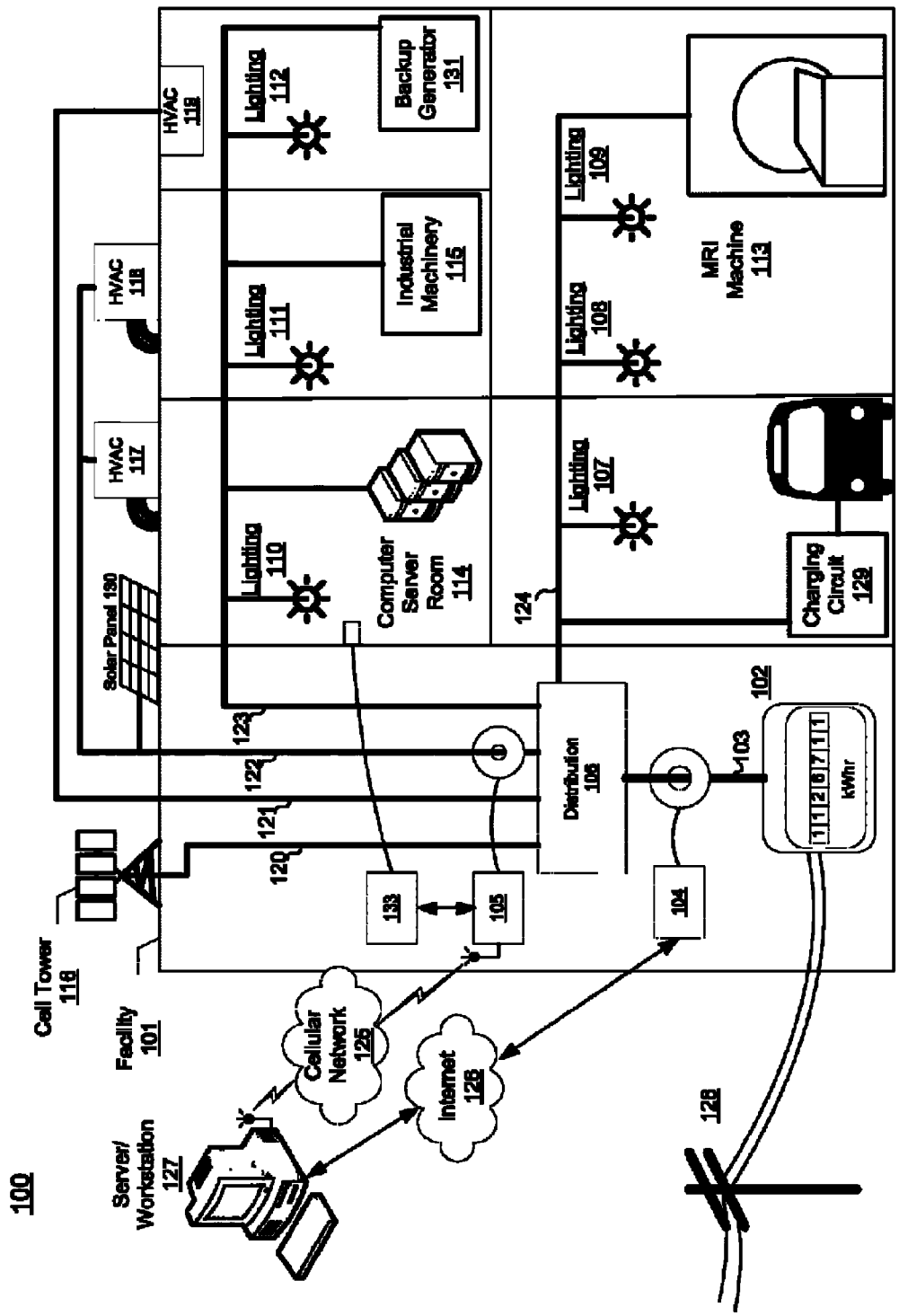
FIG. 1 illustrates an exemplary electrical distribution system of a facility in which various embodiments may be implemented.

FIG. 1 illustrates an exemplary system 100 in which various embodiments may be implemented. System 100 includes an electrical distribution system of a facility 101 in which electrical power is distributed as a consumable product to various electrical loads (i.e. users) connected to the distribution system. The facility may be commercial, residential, industrial, some combination thereof, or may be any other structure which contains a distribution system for the supply and/or generation of a consumable product. Exemplary facilities include apartment buildings, strip malls, office buildings, hospitals, industrial parks, etc.

A consumable product such as electrical power may be provided to facility 101 via any suitable source such as a public, private, and/or cooperative utility through transmission lines 128 or may be generated from on site sources such as solar panel 130, or back up generator 131. The utility may be provided as one supply feed 103 through a single meter 102, or may be supplied through several separate feeds and/or meters. Often, a single feed is split at a distribution point 106 into several separate distribution services 120-124, each of the services providing one or more different users access to the utility. Exemplary users may include loads typically found in facilities, including lighting 107-112 and/or heating, ventilation and/or air conditioning systems (HVACs) 117-119. Additional non-standard loads may also be connected to the distribution system depending on the particular use of the facility. Illustrative non-standard loads may include a computer server room 114, industrial machinery 115, medical equipment 113, and/or a cellular network tower 116. Additional exemplary non-standard loads may include charging circuits 129 in a garage associated with electric cars. Users may inductively or via a plug-in cable charge their electric cars while parked in the garage. These charges may be billed back to the individual parking tenant rather than distributed to all users in the building. Further, during peak periods, cars in the garage may be utilized to store and resource power back into the building and/or distribution network. Exemplary users may include producers of the consumable product that is put back into the distribution system for use by loads locally and/or for distribution back into the transmission lines 101. Such producers may include solar panels 130, back-up generators 131, batteries from electric cars, etc. which may be distributed about the building including on the sides, within the building, on the roof, and/or disposed around a building, cell tower, or other facility 101. These sources may be coupled to the distribution device 106 for use locally and/or input back into the system 100 via transmission lines 128.

Distribution systems may be designed to support specific users, and/or specific tenants of the facility who connect a specific group of users to the distribution system. The design of the distribution system may provide individual tenants and individual employees of the tenant their own supply feed, distribution service, and/or different combinations thereof such that use and/or generation of the consumable product by the individual tenant/employee may be uniquely measured using a meter on the tenant's/employee's supply feed or using a sub-meter on the tenant's distribution service. However, designing the distribution around specific tenants is not always accomplished or even possible. As requirements for the facility change, users of the consumable product may be added in an ad-hoc manner without accounting for how the consumable product is shared between the tenants.

In instances where access (consumption or production) to the consumable product by a specific user (load or producer), or group of users, needs to be measured on a supply feed or distribution service shared with other users, some embodiments may add a meter 104 or sub-meter 105 to a supply feed or distribution service respectively, to measure and record consumption or supply of the consumable product over time. From these measurements, analysis may be performed according to certain embodiments to determine access to the consumable product by the user, or group of users, of interest, from the total access by all the users on the measured supply feed or distribution service.

Meter 104 and sub-meter 105 may be variously configured. In one embodiment, meter 104 and sub-meter 105 may include one or more sensors coupled to the supply feed or distribution service used to measure the supply of the consumable product. Various sensors appropriate for measuring the consumption and/or supply of the consumable product will differ depending on the consumable product being measured. In an electrical distribution system in system 100, the sensor may be an inductively coupled transformer, a current shunt, or other appropriate sensor for measuring the consumable product such as power, electrical current and/or voltage. In other distribution systems for other consumable products such as natural gas and water, appropriate flow meters may be used. Meters 104 and 105 will further include a computing platform to operate the sensor, and accumulate pulse inputs (periodic measurements) from the sensors. Each meter may include several sensors and accumulate data from several different paths in the distribution system. As an example, meter 104 may include a circuit board with 10 sensor channels for sensors which may each collect pulse data in parallel. A processor on the circuit board may read each channel and accumulate data in the same and/or separate memory devices (e.g. registers) for each channel. The meter 104 may further have a data display which scrolls periodically and/or continuously to illustrate the pulses per channel. In addition to the data display, meter 104 may have buttons or other inputs which can be used for on-site programming and/or trouble shooting. After on-site programming/trouble shooting, further programming may be from a remote location and/or computer.

The meters may be variously configured. In some embodiments, the meters may transmit data (e.g., pulse data) to a different computing platform, such as server/workstation 127 via a private network (e.g., cellular network 125) and/or a public network (e.g., the Internet 126). The pulse data from one or more sensors may be individually transmitted, and/or may be grouped in any appropriate manner such as being totaled over a user defined and/or predefined and/or variable period and transmitted. The server/workstation 127 may further accumulate data from one and/or several different meters. Server/workstation 127 may be within the facility, collocated with the meters, or remote as illustrated in FIG. 1. Each meter and server/workstation may have one or more interfaces to one or more communication paths to transfer data between the meter and the server/workstation. Exemplary communication paths may include various public and private local area networks (LAN) and wide area networks (WAN), etc., over various physical networks, including voice band and digital subscriber line (DSL) modems on public switched telephone networks (PSTN), cable and fiber-optic modems and networks, cellular phone networks, satellite networks, Wifi, Wimax, etc. The various communication paths may provide a direct connection between the meters and the server/workstation, and/or may provide connection through the Internet via an Internet Service Provider (ISP). System 100 in FIG. 1 illustrates an exemplary Internet connection 126 connecting meter 104 to server/workstation 127, and an exemplary cellular phone network connection 125, connecting sub-meter 105 to server workstation 127. These communication paths could also, for example, include a combination of these networks. For example, sub-meter 105 could alternatively use any suitable wireless protocol (including 802.11a/g/n, wireless internet protocol, 3G, 4G, GSM, PHS, HCSD, TACS, CDMA, HSDPA, TDMA, CDMA2000, iDEN, TD-SCDMA, EV-DO, Mobitex, UMTS, FDMA, NMT, WCDMA, GAN, PCS, WiDEN, GPRS, PDC, WiMAX, and/or ISM band) over a network such as cellular network 125 to connect the meters to each other and/or to a public or private network (e.g., Internet 126) and to any appropriate server/workstation 127. For example, the ISM band may allow for either battery operated and/or inductively powered meters which can operate without having to be plugged in and/or connected to a wired interface and/or power. In embodiments using an Internet protocol, meter 104 may utilize a dynamic IP address, and, once powered and connected to the Internet via an Ethernet connection, may automatically find server/workstation 127 on the network and register each new channel as a new user, assigning a unique address for each channel. For example, the device may each have an auto configure and registration mode which allows the installer to remotely activate and register the device to a particular building using a laptop with a wireless card and/or a handheld smart phone like device.

The server/workstation 127 and the various meters may collect the pulse data in a variety of ways. For example, server/workstation 127 may host a website which may accumulate the pulses in one or more memories such as data registers. There may be one or more memories per sensor. Depending on the type of meter device utilized and on the type of consumable product/energy source, the data pulses and/or other signal indication may be converted to consumption (e.g. kWhr, Therm, Gallons, Lumens, etc.) on each measured supply feed or distribution service based on a programmed conversion factor. The time rate of measuring and collecting pulse data may be pre-programmed or adjusted based on such factors as the type of analysis to be done on the data, the bandwidth available to transfer the data from the meters to the server/workstation, or the capability of the meters themselves. The pulse data may be accompanied by meta-data, such as time stamps of when the pulses were measured. The data may further be protected with data encryption and/or other security measures to ensure the integrity and privacy of the data during transmission between the meters and the server/workstation 127 and during access to the data once stored in server/workstation 127. For example, the data may be encrypted and/or accompanied by a digital signature to ensure that the meters may not be altered or spoofed. An initial key exchange may occur between the meters themselves and/or between the meters and/or the workstation. In this way, once the meters are registered, the communications may not be spoofed and/or altered. Hence all reporting is done in a secure manner. Where time stamps are used, the time stamps may utilize any time base/zone, such as GMT-0 such that collection of data may be time synchronized with other measurements collected from the same distribution system and/or facility, or from other distribution systems and/or facilities.

Figure 2:
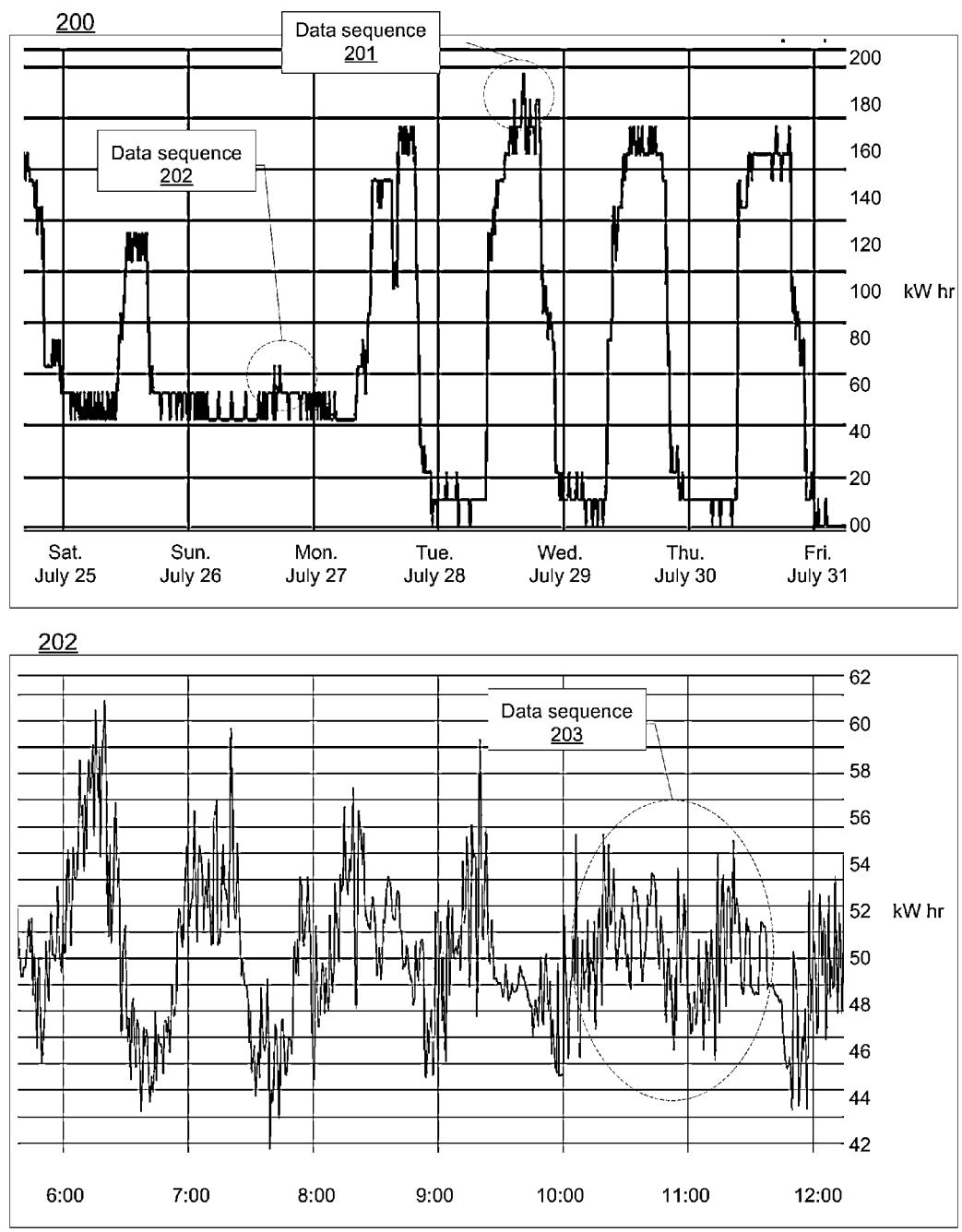
FIG. 2 illustrates an exemplary display graph illustrating data sequences representing consumption of a consumable product in a distribution system.

Once collected, the server/workstation may compile the data from each sensor/channel into time sequences of data. Exemplary data sequences may be graphically illustrated either on the meter and/or on the server/workstation 127 as, for example, illustrated in FIG. 2. This graph may also be analyzed remotely on a laptop computer, across the Internet, and/or on a smartphone. Graph 200, for example is a representative plot of kilowatt-hours (kWhr) of electrical power measured by meter 104 in FIG. 1 over a period of a week. As can be seen in FIG. 2, in exemplary embodiments, power typically oscillates during the week, with peaks reached during typical business hours and dropping during off hours and/or the weekend. Graph 200 may be variously configured including as a composite of smaller data sequences such as sequences 201 and 202. A representative graph of what data sequence 202 may look like is shown in more detail below the graph of data sequence 200. As can be seen in the graph of sequence 202, more detailed sequences, such as sequence 203 may be extracted. The detailed data sequences associated with individual meters may help pinpoint potential issues with the generation and/or use of a particular consumable resource.

Figure 3:
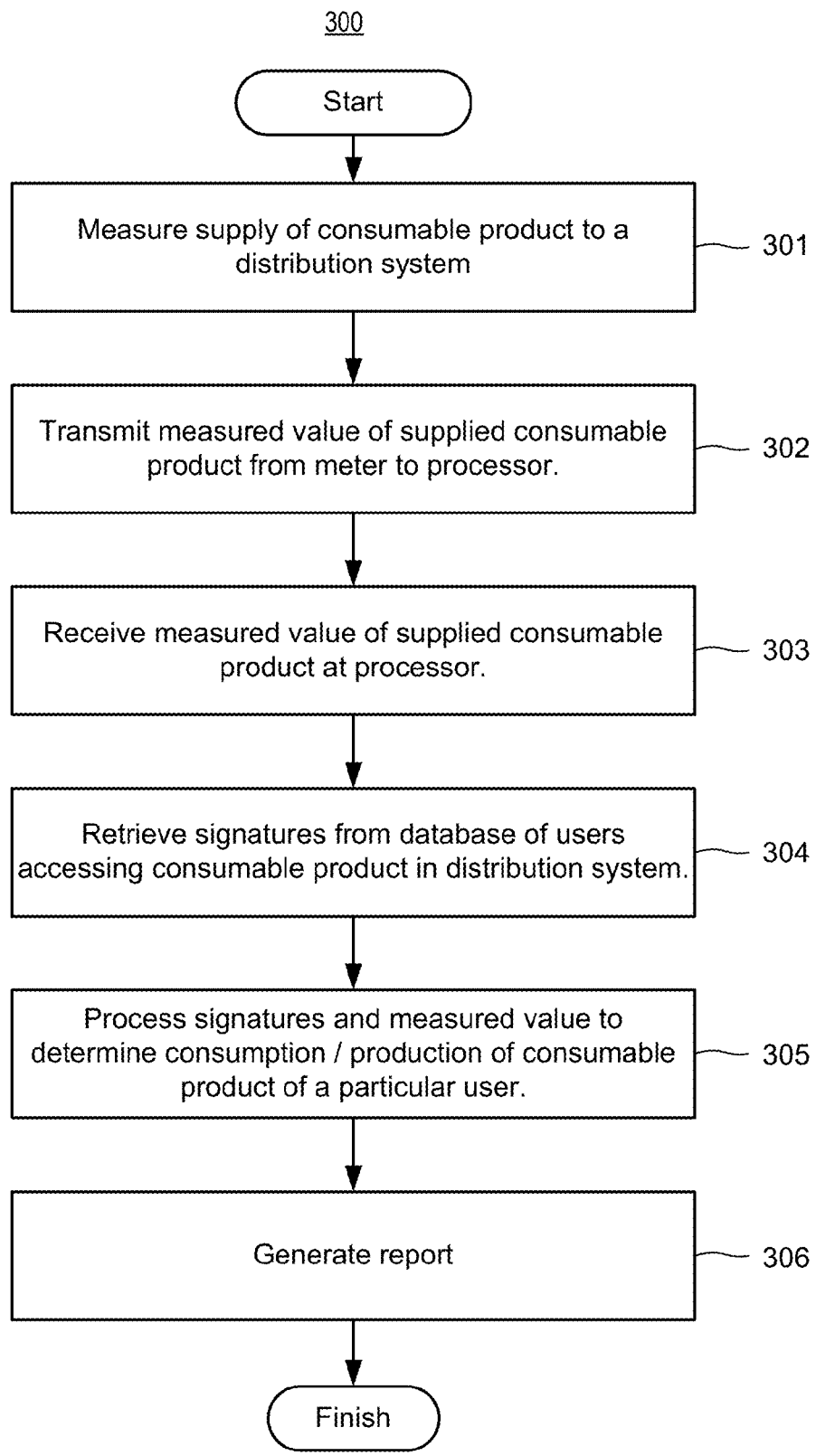
FIG. 3 illustrates a flow diagram of an embodiment for determining an amount of a consumable product accessed by a user.

FIG. 3 illustrates a process, according to some embodiments, to analyze these data sequences to determine any deviations from an expected amount of power that is consumed and/or produced by one or more particular users within a group of users connected to the measured service. Process 300 starts at 301 where the supply of a consumable product is measured in a distribution system by a meter (e.g. 104). The measured values are then transmitted from the meter in step 302, and subsequently received by a processor (e.g. server/workstation 127) in step 303. Steps 301, 302, and 303 may be accomplished as already described with respect to FIG. 1 and may result in one or more data sequences as illustrated in FIG. 2. Steps 301, 302, and 303 may occur on a pre-determined scheduled basis, as a result of the processor requesting the measured data from the meters, or both. In step 304, signatures of users are retrieved from a database. Each signature is a characterization of the access to the consumable product by one or more of the users. In step 305, the processor uses the signatures and the measured data sequences to determine which of the group of users connected to the distribution service is actually accessing the consumable product, and/or how much of the product is being accessed. Further, the consumable products consumption and/or generation from a plurality of facilities may be aggregated over time and/or over different facilities and used to formulate profile for a collection of assets. These profiles may then be used to negotiate with various suppliers of consumable products in the purchase of the consumable product. For example, an individual building owner often lacks sufficient market power to negotiate efficiently. However, using embodiments tens, hundreds, thousands, ten thousand, and even hundreds of thousands of facilities may be aggregated over the continent and over the world to negotiate the least expensive rates for consumption of the consumable products and the most favorable offsets for sources of the consumable products. In this manner, embodiments may allow the aggregation of many facilities to provide market power and to take advantage of the smart networks for consumables and the increasing deregulated environments for the delivery of consumables.

As an example of step 305, a processor in server/workstation 127 may use a pattern matching algorithm to match data sequence 203, illustrated in FIG. 2, to a signature which characterizes cell tower 116 in FIG. 1. The processor may further use more than one signature or may combine signatures to determine use of the resource by one or more users. For example, signatures for cell tower 116 and HVAC 119 may be combined additively to determine simultaneous use by 116 and 119. The processor may also manipulate the signatures and/or data sequence using various signal processing algorithms in the process of determining the users. For example, the processor may transform the signatures and data sequences from the time domain to the frequency domain using various Fourier transform algorithms. The processor may also use various artificial intelligence/smart agent/learning algorithms to process the signatures and data sequences either in the time domain and/or the frequency domain. The algorithm may also smooth the uses by filtering them with a high pass and/or low pass filter in order. In exemplary embodiments, the use of filters allows the artificial intelligence algorithms to operate more efficiently. For example, the processor may train a neural network on known operating conditions of various users, different combinations of signatures, and various data sequences acquired during the known operating conditions (with or without filtration) to develop a matching algorithm that is subsequently used in identifying later aberrations from known usage patterns.

In one exemplary embodiment, an artificial intelligence engine may implement the following algorithms:
  a. Average exceeding threshold by Standard Deviation
    1. Sample 30 minutes data;
    2. Determine if in occupied mode or unoccupied mode, determine outside temperature;
    3. Look at averages of sampled data to see if it exceeds the previous average (threshold power) by a standard deviation (either user selectable or automatically determined by past experience;
    4. In event the Threshold Power is exceeded, send email energy alarm to network administrator and/or customer including, for example, date, time and alarm type such as reading.
  b. Determine Appropriate Start and Stop times
    1. Monitor data points immediately following occupancy in the Morning start up sequence including outdoor temperature;
    2. As slope of kW line changes by an administrator configurable amount in consecutive data points (including average time windows), store the amount of change;
    3. The result may be used to alert the building owner based on the forecast of what time their building should start and compare that to what time they have in their occupancy schedule.
    4. Allows critical functions such as HVAC to be matched to actual work schedules in building.

The Artificial Intelligence Engine may constantly search the utility signatures in the database to associate a signature to a hard asset. For example: a 50 HP Fan Motor with Variable Frequency Drive may have a particular electrical consumption signature comprised of amps, power factor, watts. The AI engine may constantly review every library signature in the database (whether real or from a factory test stand—manufacturer's data) to correlate the motor signature to the library via statistical analysis. The AI engine may determine a correlation error factor between the motor signature and the library signatures (e.g. motor signature–library signature=error factor) via heuristics, optimization, simulated annealing, beam search, random optimization and/or a custom AI algorithm. When the error factor is below an acceptable level, the AI engine may output the load associated with the library signature, i.e. the 50 KW fan motor with Variable Frequency Drive.

The AI engine may thus inform an operator what load to look for. The AI engine may also write to the facility automation system sending computer code (bacnet, lontalk, any communication protocol accepted by facility automation system) to shutdown the load (50 Hp motor in this case) based on a permissive such as occupancy of facility, demand reduction, etc. In simple terms, an exemplary embodiment captures a signature measured from the distribution system and compares the measured signature to the library of signatures. The AI engine may search for Global Signatures such as for an entire facility or a sub-level within the facility (e.g. 50 KW Motor in a HVAC Unit on Roof). The comparison may be used to isolate and identify potential loads. The potential loads may then be communicated to an operator/customer or automatically controlled (e.g. on/off) via a communication protocol to regulate use of the distributed service.

Returning now to FIG. 3, the sequence will be further explained. After step 306, the processor (e.g. server/workstation 127) may then generate reports which detail the usage of the consumable product by various users and/or alerts when any user diverges from an expected usage. The report may be customized to detail access by a particular user over a fixed duration, and/or may detail a group of users of a specific tenant. The processor may further determine costs of the access by the particular user and/or group of users to the consumable product and include the cost in the report. For example, as in FIG. 1, the consumable product may be a public utility such as electrical power. Cost may simply be based on a constant rate, or may be based on a tiered utility rate which accounts for different rates at different times (i.e. peak and non-peak usage times). The reports may also include usage of a consumable product in graphical form, such as in FIG. 2. The report may further include other secondary data that may be derived from the consumable product usage. Exemplary secondary data may include calculations of green house gas emissions by a particular user. These reports may be processed as bills and sent directly to the users as well as copied to the building managers.

Process 300 may be performed by an autonomous processor that works continuously collecting data (e.g., pulse data) and determining users and/or aberrations in real-time or near real-time, and generating reports on a fixed schedule (i.e. monthly) or based on a certain level of use or cost (or aberrations in use or cost) being reached by a particular user or group of users. The reports may take the form of an invoice and sent to tenants responsible for the particular users detailed in the report. These reports may be generated and sent in the form of hard-copies and mailed, in electronic form and sent via electronic mail, text message or other form of electronic transfer, or in the form of voice messages sent via phone line. Further embodiments may allow the reports, including billing information and graphical data to be displayed on any customer interface device; desktop, laptop, PDA, Blackberry and or client internet portal, and may be further provided through a website hosted by the processor. By serving the data from a website, a tenant/customer may be able to view usage and cost data and graphic displays in real-time and/or near real-time. As referred herein, "real-time" refers to updating the usage data as it is collected and calculated with little and/or relatively little delay other than the time it takes to process the data. The amount of delay may be a designed limit on processing time, such that the data may be used in closed loop control of users, or the delay may simply be dependent on the resources available in measuring, transferring, and processing the data. For the purposes of this application, "real-time" and "near real-time" refers to the same concept in processing data.

Figure 4:
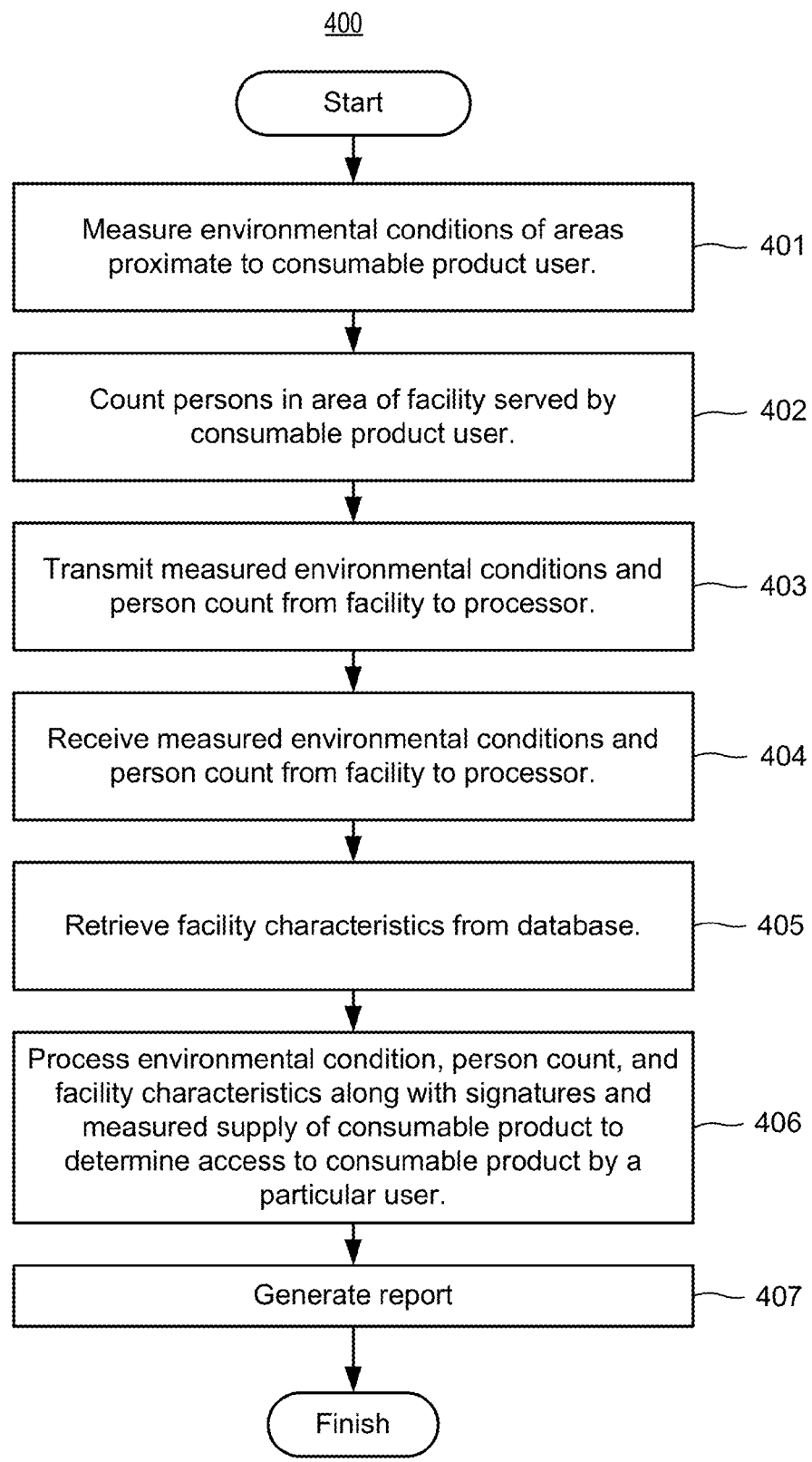
FIG. 4 illustrates a flow diagram of another embodiment for determining an amount of a consumable product accessed by a user.
Figure 5:
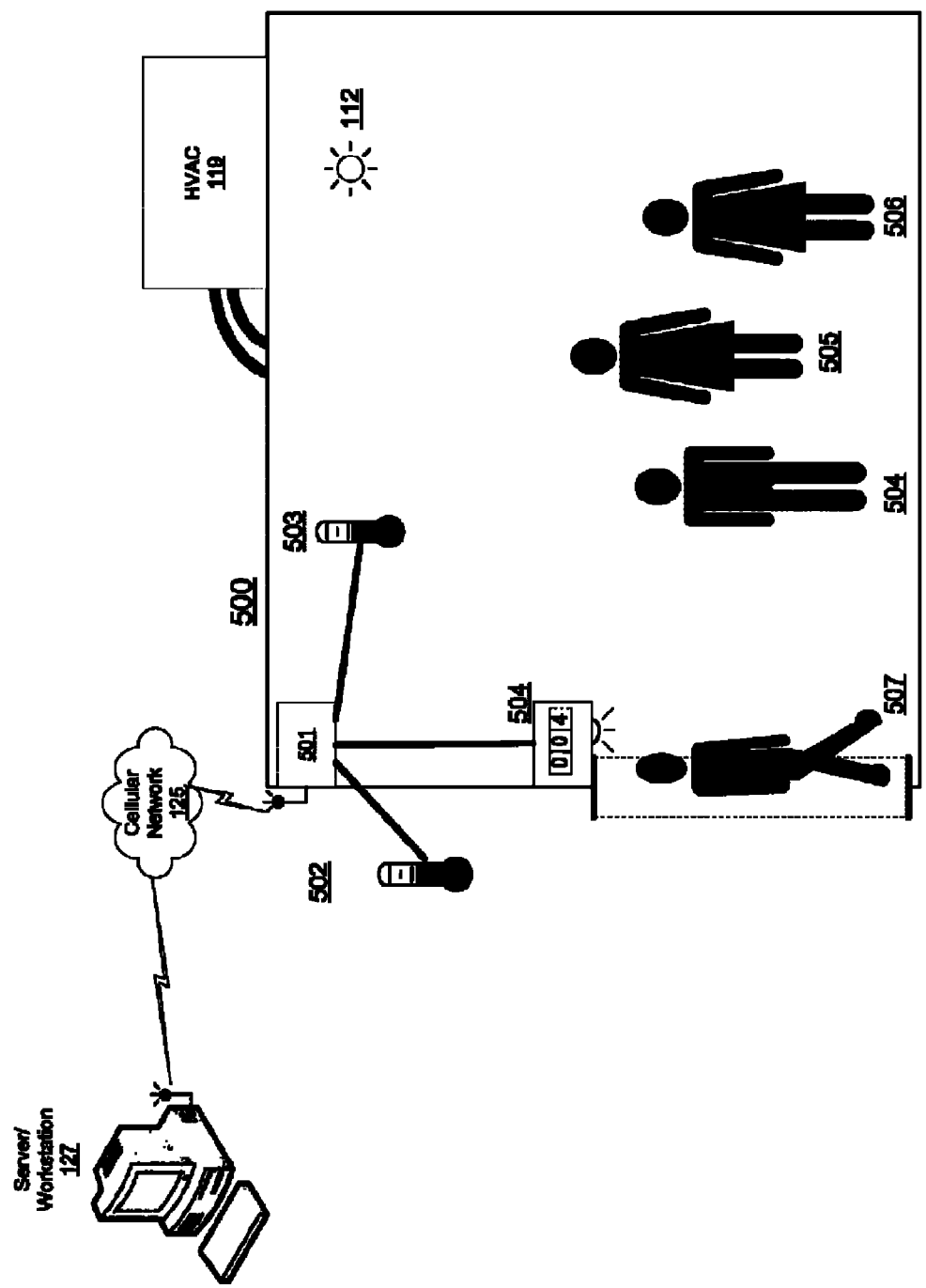
FIG. 5 illustrates an exemplary facility incorporating various sensors which may be used with various embodiments.

Process 300 may be augmented with additional steps of process 400 illustrated in FIG. 4, and described with respect to FIG. 5, for incorporating operating conditions into the determination of the various users. In this exemplary embodiment, Process 400 starts at 401 by measuring environmental conditions of areas which are proximate to a particular user or are served by a particular user. For example, as illustrated in FIG. 5, HVAC 119 and lighting 120 may serve a room 500 in the facility 101 of FIG. 1. Environmental conditions such as temperature 503 inside of the room and temperature 502 outside of the room may be measured. Other operating conditions which affect usage of the consumable product may also be captured, as in step 402 for example, where persons within room 500 may be counted by a sensor 504. Such measurements of operating conditions may be accompanied by meta-data such as time stamps or time intervals such that the operating conditions may later be correlated to usage data of electrical power by users 119 and 120. In step 403, the measured environmental and other captured operating conditions are transmitted to the processor. FIG. 5 illustrates an exemplary data collection node 501 collecting the measured values and transmitting them to the processor in server/workstation 127 through cellular network 125. Data collection node 501, may be the same as meters 104 and 105, or may be some other computing platform operating in the same manner as 104 and 105 over the same types of communication links to transfer data to server/workstation 127. In step 404, the processor in server/workstation 127 receives the transmitted data. In addition to receiving operating conditions measured from the facility, the processor may retrieve other operating conditions from a database such as in step 405. The processor, in step 405, may retrieve facility characteristics from the database, such as square footage of rooms in the facility; age of the facility; insulation factors of walls, windows, and other structures; load factors which indicate peak usage versus minimal usage ratios, historical seasonal usage information, age and efficiencies of the users, etc. In step 406, the same steps as in steps 301 to 305 of process 300 are performed except that the operating conditions measured from the facility and retrieved from the database are incorporated in to the step 305 for determining access to the consumable product by a particular user. In step 407, a report may be generated in the same manner as in step 306 of process 300. The report may further include details of the operating conditions acquired in steps 401 to 405, and other secondary data that may be derived from the operating conditions and consumable product usage. Exemplary secondary data may include calculations of green house gas emissions by a particular user.

As with process 300, the steps of process 400 may be performed autonomously, in which the operating conditions and usage data are continuously collected, users are determined in real-time or near real-time, and reports are generated on a fixed schedule (i.e. monthly) or when certain levels of usage or costs are reached by a particular user or group of users.

Figure 6:
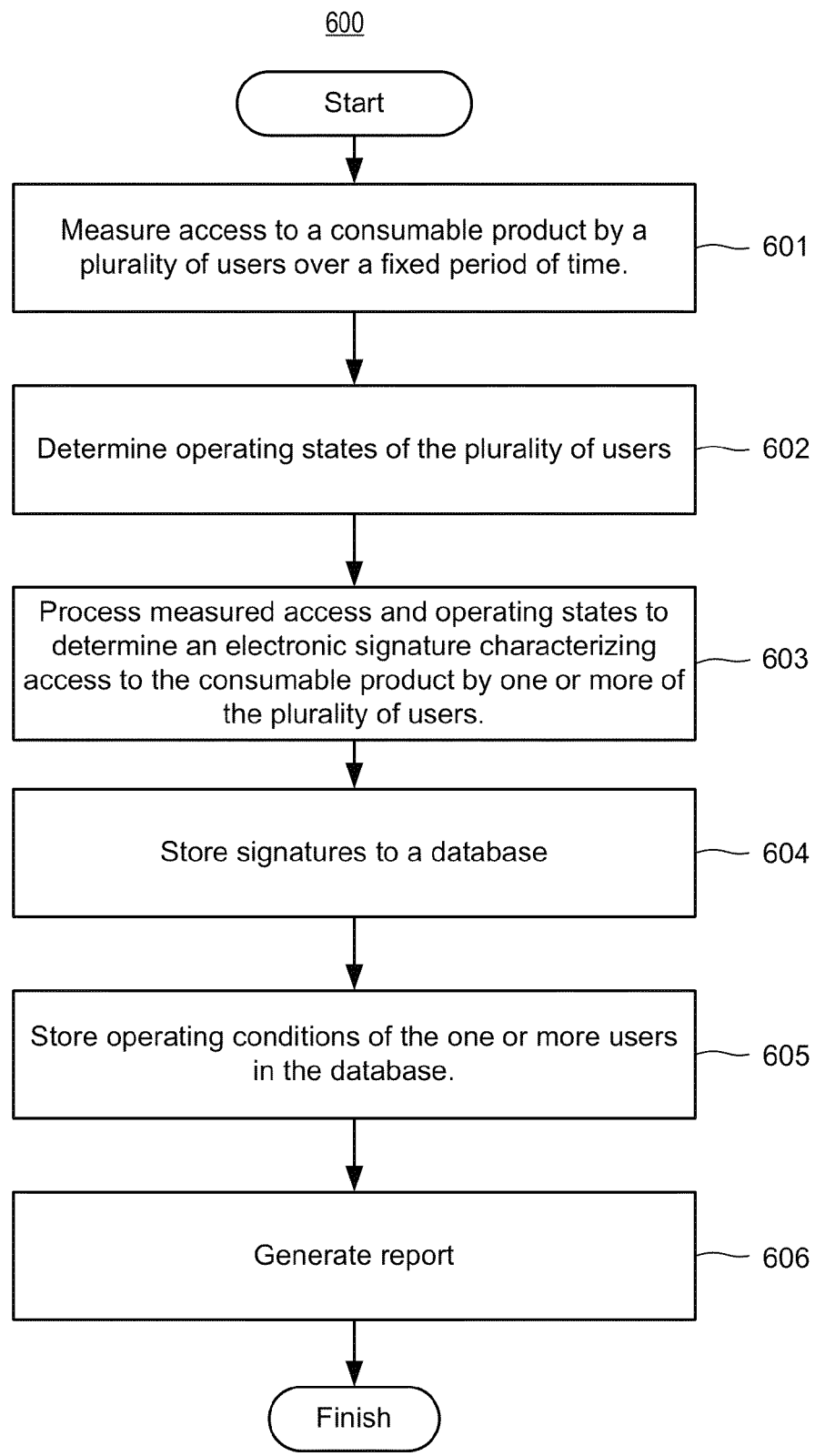
FIG. 6 illustrates a flow diagram of an embodiment for determining signatures which characterize access to a consumable product by one or more users.

In order to perform processes 300 and 400, the processor performing the process it may be desirable for the processor to have either preloaded and/or learned signatures of the various users connected to the distribution system. In another exemplary embodiment, the processor may create these signatures according to a process 600 as illustrated in FIG. 6. In one exemplary embodiment, Process 600 in FIG. 6 starts by measuring access to a consumable product by a plurality of users on a supply feed or a distribution service over a fixed period of time. During the measuring, the operating states of the plurality of users are also determined. The operating states may be determined by monitoring the users or controlling the users. The monitoring and controlling may be performed by the processor using the same or similar communication links used for receiving data from meters. Other operating conditions may also be monitored or measured over the fixed period of time. The operating conditions may include the same measured (e.g. inside and outside temperature, person count, etc.) and facility characteristics (e.g. square footage, facility age, insulation factors, load factors, historical seasonal usage information, age and efficiencies of the users, etc.) as in process 400. Measuring access to the consumable product and monitoring the operating conditions may be achieved by the same or similar manner as is accomplished in processes 300 and 400. Once access to the consumable product and operating conditions are measured or determined, the data is correlated to the known operating states to determine the signatures which characterize the access by one or more users of the plurality of users. The signatures may contain variables to account for different operating conditions or may assume an average or estimated operating condition. Multiple signatures may further be created for the same on or more users, with each signature reflecting a different set of operating conditions.

The creation of signatures may be accomplished by a variety of different algorithms. For example, referring back to FIG. 2, data sequence 203 may have been recorded when HVAC 119 was being cycled on and off, lighting 112 was being powered during regular operating hours of the facility, and cell tower 116 was operating. A processor in server/workstation 127 may use a pattern matching algorithm to correlate transitions in data sequence 203 to the changes in states of HVAC 119, lighting 112, and cell tower 116 to create signatures which characterize each of these loads or a combination of these loads. Previously determined signatures (e.g. for lighting 112 and HVAC 119), may be used to cancel out the effects of certain loads (e.g. lighting and HVAC) in determining a signature of just one of the users (e.g. cell tower). In this manner, the signature may be combinable or divisible to uniquely reflect use of the consumable product by a combination of users on a single supply feed or distribution service. The processor may also manipulate the data sequence and state information using various signal processing algorithms in the process of determining the signatures. For example, the processor may transform the data sequences from the time domain to the frequency domain using various Fourier transform algorithms. The processor may also use various artificial intelligence/intelligent agents/learning algorithms to determine the signatures. For example, the processor may train a neural network on known operating conditions, operating states, and measured data sequences to determine the sequences. The signatures may take on a plurality of forms, including a time sequence of data or a frequency spectrum of data that may be combined with other signatures to be matched to measured data sequences. In the case of using a neural network to identify a user in process 300 and 400, the signature may be in the form of branch weights in the neural network for identifying a particular combination of users.

After determining one or more signatures, the signatures may be stored in a database at step 604. In addition to storing the signatures, the measured or determined operating conditions may also be stored to the database in step 605. The signatures and operating conditions may be stored in a single database, or may be stored in separate and numerous databases. The databases may be collocated with the processor, or may be remote and accessed by the processor through a network connection. Process 600 may finish with generating a report of the stored signatures and operating conditions. The databases may then be used, for example, in processes 300 and 400 for later determining access to the consumable product by a particular user. In the example of FIG. 1, the various signatures would reflect various electrical loads and sources as already described. The database of signatures may also be used in other processes such as determining energy ratings of users or compliance of different users and facilities with applicable governmental regulations, or trade group certifications.

Figure 8:
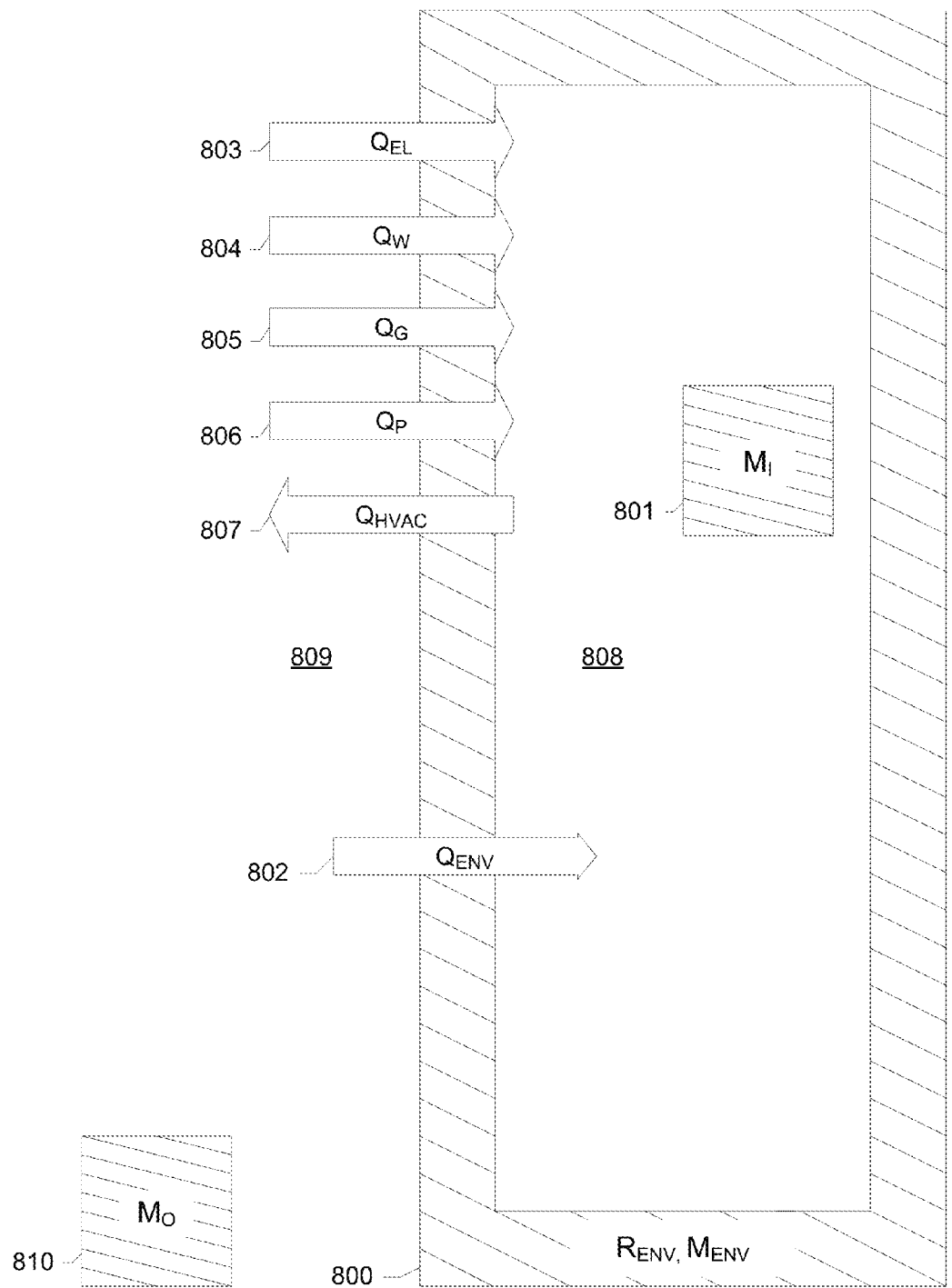
FIG. 8 illustrates a building envelope in which various embodiments may be implemented.

In addition to determining energy usage by users within a facility, determining energy performance of the facility may also be used in various embodiments. FIG. 8 illustrates a building envelope 800 of a facility in which energy performance may be determined. Building envelope 800 may include the building structure, which thermally separates an enclosed volume from an outside environment. The structure may include, for example, any combination of building material (e.g., cement, glass, wood, metal, etc.), and may be used for any purpose (e.g., residential, commercial, industrial, etc.). For simplicity, building envelope may be shown schematically to include a solid perimeter with a single enclosed space, but the building envelope may also include floors, ceilings, and any other structure which encloses the volume of interior space.

Various aspects of building envelope 800 described herein may also apply equally to multi-room structures, a single room within a multi-room structure, a single floor within a multi-floor structure, structures with openings such as doorways, vents, windows and other fenestration, structures with ceilings of various heights, structures with various shaped perimeters, and/or structures with walls, floors, and ceilings of different shapes and sizes.

One function of building envelope 800 is to provide thermal isolation between an outside environment 809 and inside environment 808, such that the inside environment 808 may be controlled in an energy efficient manner. Although, generally, the outside environment 809 comprises the space outside of the entire building structure, outside environment 809 may equally refer to one or more rooms or spaces within the building structure bordering a building envelope which encloses only portion of the building structure and/or to adjacent buildings where, for example, the building abuts an adjacent building. The building envelope may, for example, enclose a group of one or more rooms, or a single floor.

Determining energy efficiency of a building may include determining the thermal properties of the building envelope. In particular, where a building envelope has a thermal mass, the building may have several components of induced and residual heat flow through the building envelope.

Thermal mass (e.g., heat capacity) may be considered to be the property of an object to store heat and may be measured in Joules per degree Celsius (J/° C.), in British Thermal Units per degree Fahrenheit (BTU/° F.), and/or equivalent. The thermal mass of an object may depend on the specific heat capacities of the materials making up the object. Specific heat capacity, denoted C, is often considered the materials heat capacity per unit of the material, and may be specified per mass (e.g., BTU/[° F.×$lb_m$]), and/or per volume (e.g., BTU/[° F.×$ft^3$]). Dense objects, such as brick and stone, typically have a greater capacity to store heat than less dense objects, such as wood or foam insulation. The building envelope's thermal mass, $M_{ENV}$, will be a function of the material making up the buildings structure.

In addition to the $M_{ENV}$ of the building envelope, thermal mass may also be present within the inside environment, represented as object 801 having thermal mass $M_I$, and within the outside environment, represented by object 810 having a thermal mass $M_O$. Objects 801 and 810 may each represent a single object, or may each represent a composite of the thermal masses of multiple objects. Inside object 801, for example, may include furniture, equipment, vehicles, people, warehoused goods, and other movable or permanently affixed structures. Outside object 810 may include other buildings, building structures, roadways, and other movable and affixed objects.

Various embodiments include determining heat flow through and/or into the building envelope. FIG. 8 includes various illustrative examples of heat flow shown as heat paths 802 to 807 having respective heat flows $Q_{ENV}$, $Q_{EL}$, $Q_W$, $Q_G$, $Q_P$, and $Q_{HVAC}$. Heat flow is often the quantity of heat energy transferred per unit of time (e.g., W=J/s, BTU/Hr). Related to heat flow, heat flux, denoted $Q'$, may be defined as the quantity of heat per cross-sectional unit area, and may be measured in watts per meter squared ($W/m^2$), and/or other equivalent units. The heat paths shown in FIG. 8 may move heat between the outside environment 809 and the inside environment 808 and between the environments and the thermal masses $M_{EV}$, $M_I$ and $M_O$. Various embodiments include tracking of heat flow along the various induced paths periodically over time.

Heat path 803-807 often represent induced heat flow, and heat path 802 often represents a residual heat flow. Induced heat flow may be the result of supplying or injecting energy sources into the building envelope, which may then produce heat through the sources consumption (i.e., a consumable product). Examples of energy sources include electricity, fossil fuels, and people. Induced heat flow may also result by mechanical means, such as heating, ventilation, and air conditioning (HVAC) systems, which often mechanically move heat in or out the building envelope to control the climate within the building envelope.

Heat path 803, $Q_{EL}$, of FIG. 8, represents heat flow produced by electrical power supplied to the building envelope. In various aspects, electrical power may be measured and/or its distribution monitored as described with respect to FIG. 1 in order to determine heat produced from its use within the building envelope.

Referring back to FIG. 1, heat flow 803, $Q_{EL}$, into the building envelope may depend on the distribution and use of the electrical power. The distribution system itself, consisting of distribution point 106, and services 120-124, has electrical resistance and may have a power loss in the form of heat according to the equation of $P=I^2*R$, where P is the power consumed, I is the current passing through any particular path, and R is the resistance of the path. Heat may also be produced in various forms by the end load. For example, lighting 107-112, may produce heat that is predominantly radiation heat, while computer equipment in computer server room 114 may heat the interior environment predominantly through conduction and convection. Other loads, such as charging circuit 129 may not convert all of the electrical power into heat, but may instead store the power in batteries, fuel cells, or other storage device. Still, other loads may convert some of the electrical power into mechanical work.

In various aspects, heat flow 803, $Q_{EL}$, is determined by measuring the flow of electrical power through one or more meters and sub-meters, such as 102-105, and/or by monitoring one or more loads, such as light/load meter 133 monitoring lighting 110. It should be noted that the various loads and distribution paths, such as HVACs 117-118, cell tower 116 and portions of services 120-122, may be outside of the building envelope, and thus, would not add heat within the building envelope environment.

Heat path 804, $Q_W$, in FIG. 8 may be another source of induced heat flow produced by the flow of water through the building envelope. Like all matter, water has the ability to store heat, and has a heat capacity of 1 BTU/[° F.x$lb_m$] (approximately 4.2 J/(g*K)). As water flows through a building envelope, the water may transfer heat to or from the inside environment and/or the thermal mass of the building envelope. In many situations, the amount of heat transfer from water may be negligible, but in various embodiments, water has a non-insignificant effect. For example, in hotter climates, water which has been cooled through supply lines underground, may draw heat from the inside environment 808 as the water passes through pipes or through radiators within the building. In other embodiments, hot water used to heat numerous buildings in a campus system may be piped into a building envelope and through radiators to dissipate the stored heat within the building envelope. In yet other embodiments, water which has been heated within the building envelope by heat produced from another energy source may carry heat from the building envelope through drain pipes. In various embodiments, water flow and temperature may be monitored in and/or out of the building in order to calculate a heat flow 804, $Q_W$, resulting from the water flow.

Heat path 805, $Q_G$, in FIG. 8 provides another source of induced heat flow produced by the flow of fossil, bio, or synthetic fuels. The fuel may be a gas, such as natural gas, biogas, propane, butane, etc., may be liquid, such as compressed natural gas, liquid propane, gasoline, kerosene, diesel, etc., or may be solid, for example coal, wood, etc. Like water, heat flow may result from the heat capacity of the fuel itself storing energy, transferring heat in or out of the building envelope directly as a result of the fuel flow. Accordingly, in various embodiments, temperature and fuel flow in and/or out of the building are monitored by one or more meters to calculate a heat flow $Q_G$ resulting from the heat capacity of the fuel.

Like electricity, the heat path 805, $Q_G$, may also result from fuel flowing into the building environment, and then being consumed to produce heat. For example, a building may have a natural gas utility supply used for water heating, furnaces, clothes dryers, cooking, and other various functions. The heat flow $Q_G$ resulting from consuming the fuel will depend on the quantity of fuel consumed and energy conversion efficiency of each particular application within the building envelope. Accordingly, one embodiment monitors distribution of the fuel to various consumption points within the building envelope, and determines heat flow based on known, estimated, or measured energy conversion/efficiency factors. For example, natural gas has a known energy conversion factor through combustion (e.g., 1000 BTU/$ft^3$). In a cooking application using natural gas, one embodiment may monitor the quantity of gas consumed by a stove and use the known energy conversion factor to determine heat transfer into the building envelope. In the same system, exhaust vents over the stove may be monitored to determine air temperature and flow from the cooking area to determine heat flow leaving the building envelope through the exhaust. In various embodiments, the heat path induced by the exhaust may be included in the heat flow calculation $Q_G$, or may be calculated as a separate heat flow factor. The heat flow resulting from the exhaust would be determined in the same way as water based on flow rate, temperature, and heat capacity of the exhaust.

Heat path 806 having heat flow $Q_P$ includes another source of induced heat flow resulting from the moving of self contained heat emitting bodies being moved in and out of the building. The most typical self contained heat emitting bodies are people moving in and/or out of the building. In various embodiments, doorways and other entrances to a building envelope are monitored to count people entering or exiting. The monitoring may exist only for building entrances, or may occur per floor, or per room. Each person's contribution to heat flow $Q_P$ may then be determined by estimating heat emission based on an average person. In another embodiment, heat emission estimates of each person may be based on more detailed monitoring which determines size, height and/or weight of persons entering and exiting the building, room, or floor. In yet another embodiment, each person's heat emission may be estimated based on the amount of activity each person exerts, which may be measured, for example, by using motion sensors. In yet another embodiment, thermal detectors or cameras may measure a person's heat signature or heat output to determine that person's contribution to $Q_P$.

Although $Q_P$ is described with respect to people, the same embodiments may equally be applied to other illustrative self contained heat emitting bodies such as other animals. In yet another embodiment, the self contained heat emitting bodies may include automobiles moving in and out of parking garages or other spaces within the building envelope. In monitoring the automobiles, various embodiments may treat the automobile, drivers, and passengers as one heat emitting body, or may distinguish each automobile, driver, and passenger as separate heat emitting bodies and/or based on the size and type of the automobile.

Heat path 807 having a heat flow $Q_{HVAC}$ represents heat flow induced by Heating, Ventilation, and Air Conditioning (HVAC) systems. HVAC systems, such as a heat pump, typically mechanically move heat in or out of the building envelope to control the climate inside the building envelope. In various embodiments, an HVAC system may include electric heaters, natural gas furnaces, hot/chilled water circulation, or other systems, which create heat paths that include previously described heat paths, such as $Q_{EL}$, $Q_W$, or $Q_G$. For example, an HVAC system with electric heaters would generate heat directly from an electric utility service as described above with respect to $Q_{EL}$. In these embodiments, the heat path may be considered as either $Q_{HVAC}$ or as one of the other described heat flows. In other various embodiments having an HVAC system such as an air conditioning system or a heat pump, electricity or other energy source may be converted into mechanical energy to create a separate heat path which forces heat in or out of a building envelope.

In various embodiments, heat flow $Q_{HVAC}$ may be determined by directly monitoring input and/or outputs of the HVAC system. For example, in a forced air furnace, intake and outtake airflow, along with temperature of the intake and outtake air may be measured with one or more meters to calculate the heat output of the furnace. In other embodiments, the energy source (e.g., electricity) supplying the HVAC system may be monitored, and an estimated, measured, or manufacture supplied conversion/efficiency factor may be applied to determine the heat movement through the building envelope based on the measured energy source.

As shown in FIG. 8, in addition to the induced heat paths heat paths 803 to 807 having respective heat flows $Q_{EL}$, $Q_W$, $Q_G$, $Q_P$, and $Q_{HVAC}$, a building envelope may also have a residual net heat path 802 having a heat flow $Q_{ENV}$. Heat flow $Q_{ENV}$ often depends on the insulation properties of the building structure.

In a simple embodiment, heat path 802 may be predominantly through conduction of the building envelope and can be characterized by a composite thermal resistance, or $R_{VALUE}$, of the material that makes up the building structure. $R_{VALUE}$ for a particular material is described by the equation $R_{VALUE} = (T2-T1)/Q^f$, where $T2-T1$ is the delta temperature on either side of the material and $Q^f$ is the heat flux, or heat flow per unit area, through the material. $R_{VALUE}$ for many materials is well known and provided by the manufacturer.

Figure 14:
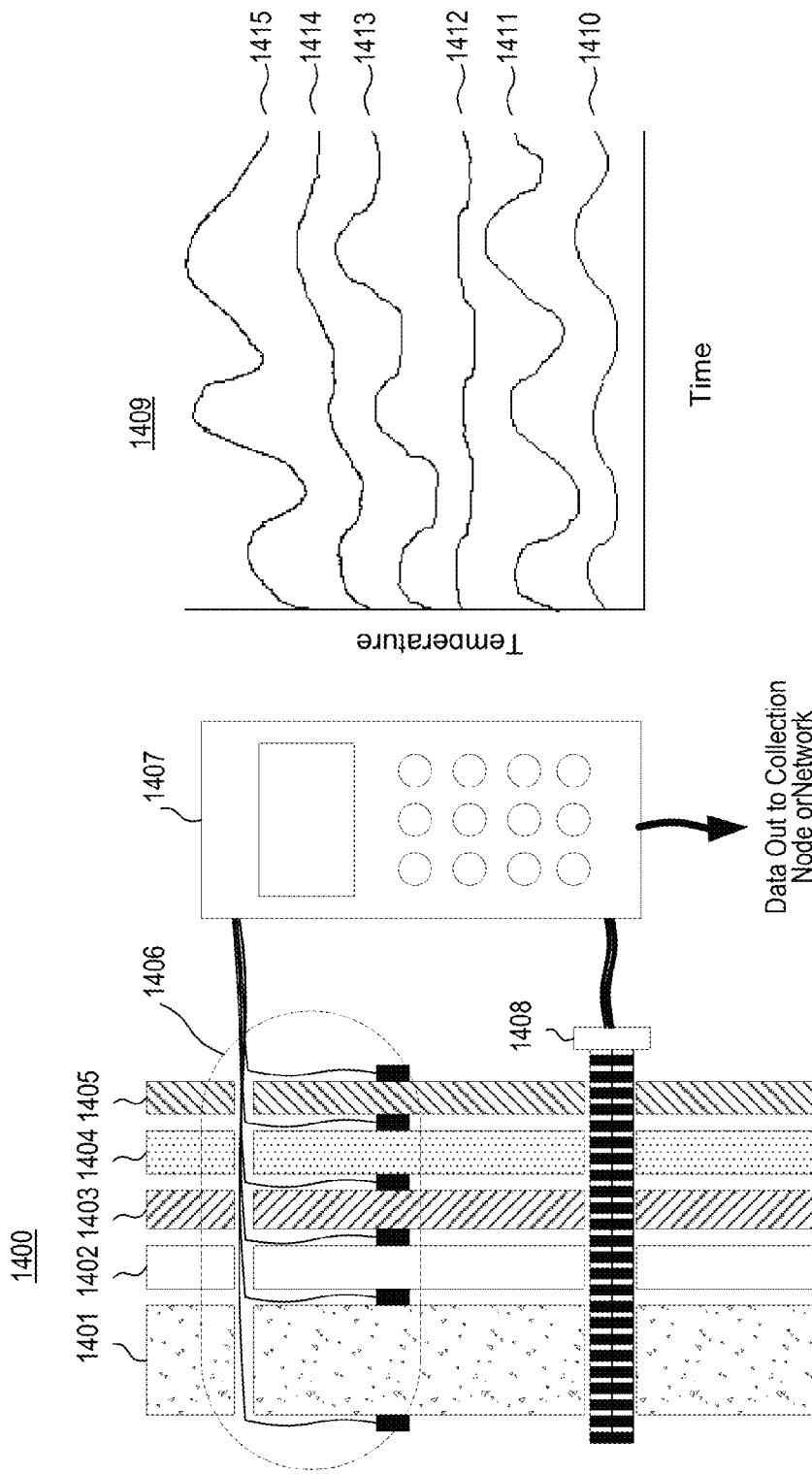
FIG. 14 illustrates various embodiments of sensors and resulting sensor data.

Often, the building structure may not be a single material, but a composite of multiple materials in layers. For example, as shown in FIG. 14, a cross-sectional view of a building wall 1400 may include an outside concrete layer 1401, next to a thin air layer 1402, followed by a sheathing layer 1403, an insulation layer 1404, and a drywall layer 1405. In this example a composite $R_{VALUE}$ would be calculated as $R_{VALUE} = R_{VALUE(CONCRETE)} + R_{VALUE(AIR)} + R_{VALUE(SHEATHING)} + R_{VALUE(INSULATION)} + R_{VALUE(DRYWALL)}$. In practice, wall construction is typically more complicated and may include many more parts such as wooden or metal studs, epoxies, nails, pipes, etc. To determine $R_{VALUE}$ of complicated wall assemblies, a weighted average of each $R_{VALUE}$ of each material may be used, or the composite $R_{VALUE}$ may be computed using modeling software of the wall assembly.

Figure 9:
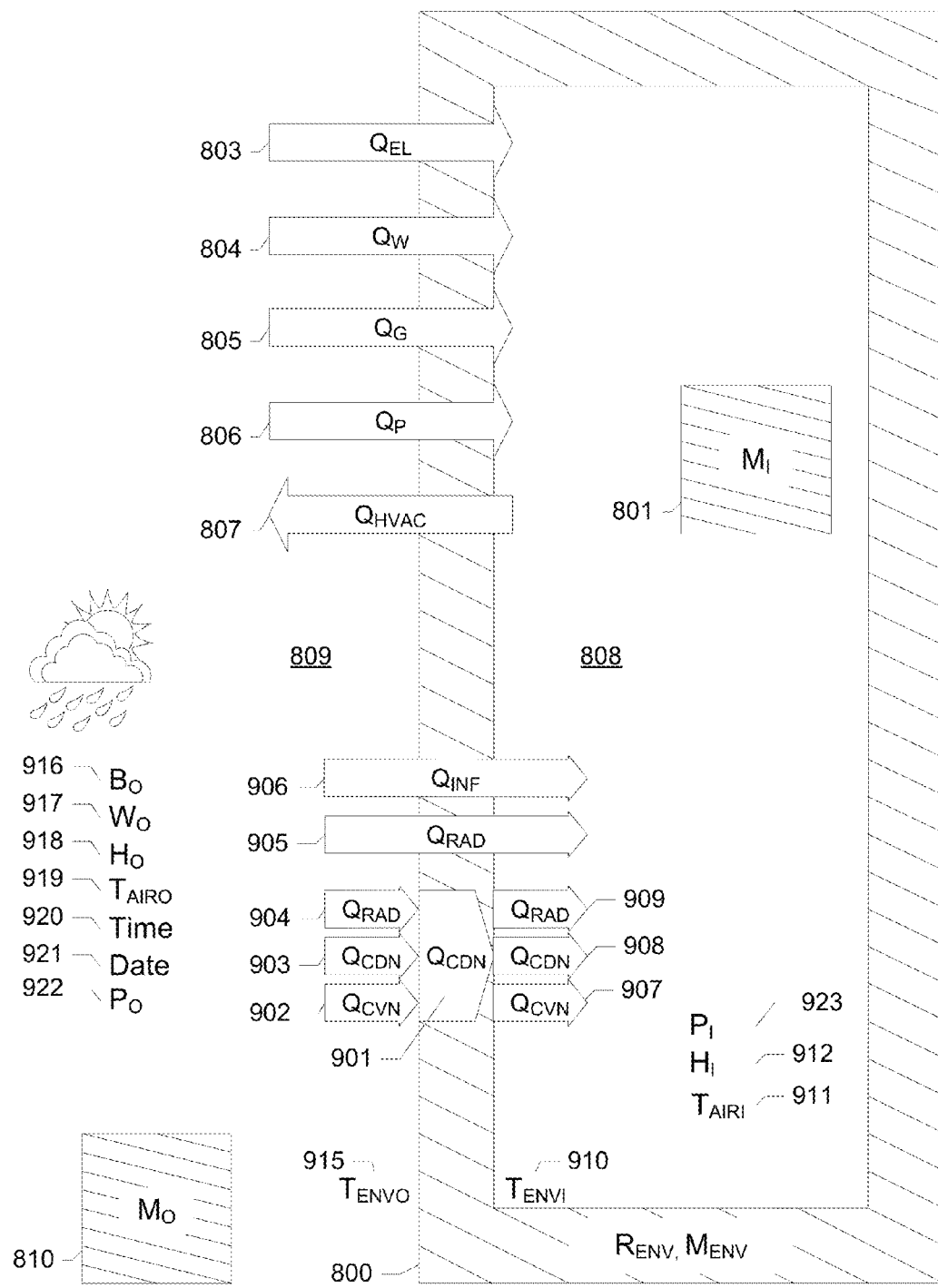
FIG. 9 illustrates heat flow through a building envelope in which various embodiments may be implemented.

In many buildings, $R_{VALUE}$, based on conduction alone is insufficient since many more factors contribute to the residual thermal path 802. Radiation and convection from the atmosphere also play a role, as well as air infiltration through doorways, windows, vents, and cracks. FIG. 9 illustrates the building envelope of FIG. 8, but replaces thermal path 802 with a more comprehensive illustration of residual thermal paths 901 to 909. In FIG. 9, thermal path 901 having heat flow $Q_{CDN}$ represents the conduction thermal path previously discussed. Heat flow $Q_{CDN}$ will depend on $R_{ENV}$, the $R_{VALUE}$ of the building envelope, and on the temperatures $T_{ENVI}$ and $T_{ENVO}$, which often are the inside and outside surface temperatures 910 and 915 respectively of the building envelope. $T_{ENVI}$ and $T_{ENVO}$, in turn, may be determined by heat transfer from the inside and outside environments 808 and 809, through radiation, conduction and convection.

In the outside environment, radiation from the sun, represented by $Q_{RAD}$ may be determined predominantly by the sun position, obstructions which block the sun, atmospheric conditions such as cloudiness and green house effects, and reflectivity of the building surface. Time 920 and Date 921 may be used to determine sun position. Weather forecasts and models may be used, or direct measurements may be made at various locations on the outside of the building envelope, to determine atmospheric conditions such as brightness 916. From these factors, radiation hitting the building envelope may be determined. The determined radiation along with the known reflectivity of the surface may then be used to determine heat energy transferred to the outside surface and/or the lower temperature space or zone.

In addition to outside radiation, heating of the building envelope's outside surface occurs through conduction 903 and convection 902 having heat flow $Q_{CDN}$ and $Q_{CVN}$, respectively. Heat transfer through conduction can be determined by the difference between the air temperature 919 and building surface temperature 915 having temperatures $T_{AIRO}$ and $T_{ENVO}$ respectively, and the respective thermal masses (i.e., heat capacities) of the air and building envelope. The thermal mass of the air may vary with humidity 918 ($H_O$) and barometric pressure 922 ($P_O$). Heat transfer through convection 902 is affected by the same factors as conduction path 903, but may further be affected by atmospheric conditions such as wind 917 ($W_O$).

In the same ways that heat is transferred from the outside environment to the outside surface of the building envelope, heat may be transferred from the inside surface of the building envelope to the inside environment through radiation heat path 909, conduction heat path 908 and convection heat path 907.

Radiation may also enter the building envelope directly through heat path 905, $Q_{RAD}$, which may comprise openings such as doorways, windows, and/or other fenestration. Open doorways would provide no resistance to radiation entering, whereas windows will typically have a designed emissivity (e) which is a measure of the amount of radiation reflected, and thus prevented from entering the building envelope.

Building envelope may also have a residual heat path 906, $Q_{INF}$, resulting from air infiltration through openings in the building envelope. Heat path 906 has a representative thermal flow $Q_{INF}$, which may be determined by the cross section and positions of openings, and environmental factors such as outside wind $W_O$, inside and/or outside humidity, 918 ($H_O$) and 912 ($H_I$) respectively, and/or inside and/or outside barometric pressures, 922 ($P_O$) and 923 ($P_I$) respectively.

Building envelopes are generally designed to minimize the thermal paths 901-909 shown in FIG. 9. As previously discussed, as-built structures may not and often do not meet the insulation performance of a planned design after completion. Errors in the designed thermal performance may be caused by design variations that are not reflected in a model, construction of the structure which is not to specification, incorrect assumptions on building usage and weather, utility equipment which is not installed correctly or functioning according to specification, insufficient model fidelity, and numerous other factors. Further, a building's energy performance may change over time due to the aging of materials, modifications to building structures and systems, or damage to the structures.

In addition, thermal mass $M_{ENV}$ of the building envelope may impact the thermal performance of the building envelope by serving as a heat reservoir for some of the conducted heat through the building envelope, thereby damping or adding a time delay to the conducted heat transfer between the inside and outside environments. Likewise internal object 801 and external object 810 may have the same effect in dampening variations in the inside and outside temperatures 911 and 919 respectively. For example, a house in the countryside will be in the presence of a vastly different outside thermal mass than that of an office building within a heat island of a dense city, and thus the outside temperature of the building in the city may be higher. Further, objects 801 and 810 may be moved, or new objects erected, such as constructing new adjacent buildings. Because objects 801 and 810 may be moved or erected, their thermal impact on building envelope 800 may change over time.

Figure 10:
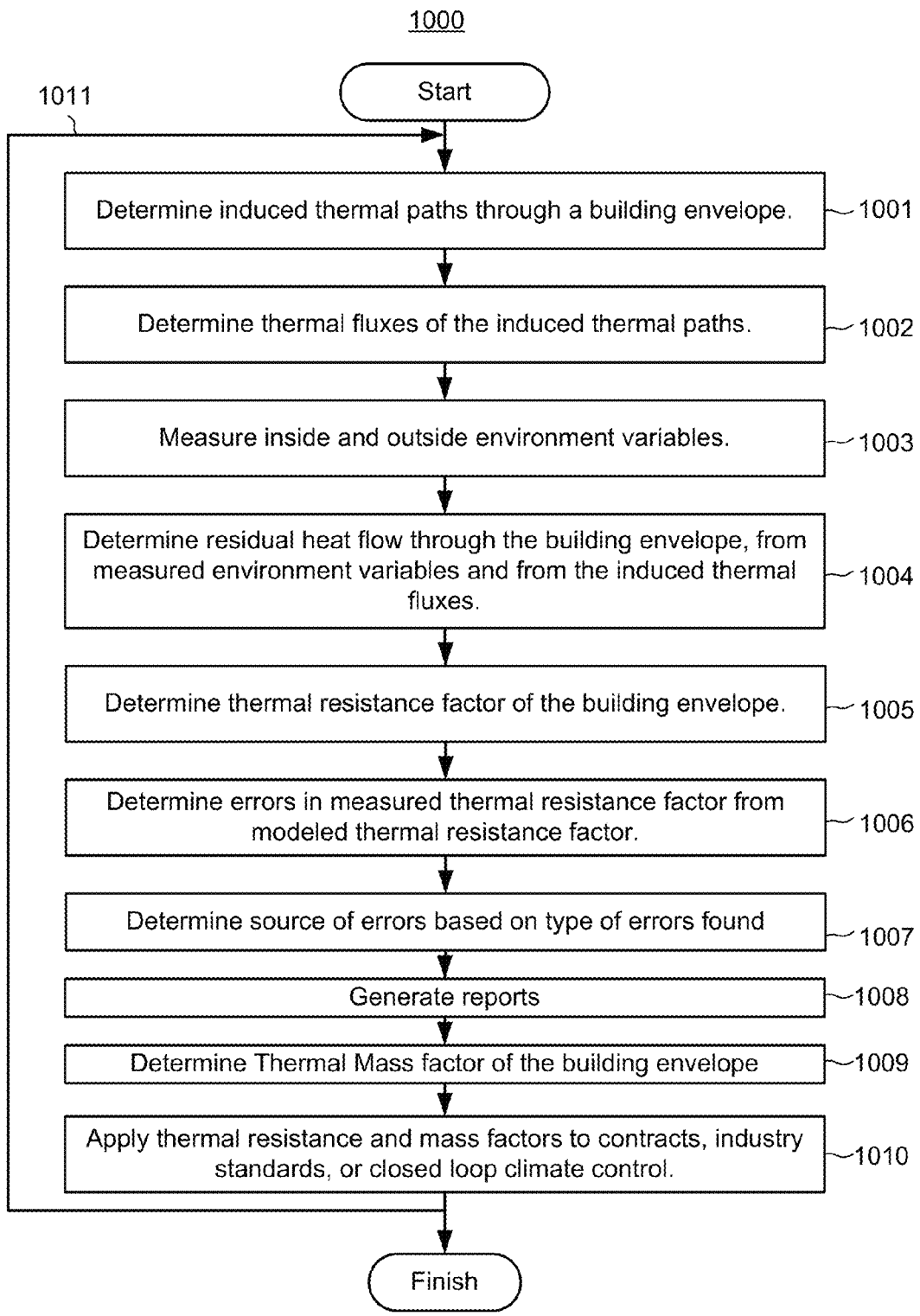
FIG. 10 illustrates a flow diagram of an embodiment for determining heat flow and thermal performance of a building envelope.

Because of errors in the designed thermal performance and the change in performance over time, various embodiments may periodically determine the actual residual heat flow through the building envelope. In one embodiment, heat flow and thermal performance of a building envelope are determined by process 1000 as shown in FIG. 10. In step 1001, induced thermal paths 803-807 are determined as discussed above through monitoring and measurement of the various energy sources entering and leaving the building envelope. In step 1002, resultant induced thermal flows $Q_{EL}$, $Q_W$, $Q_G$, $Q_P$, and $Q_{HVAC}$ are calculated as disclosed above. In step 1003, the inside and outside environments are measured. The measurements may occur periodically at fixed time intervals, may occur in real-time, and may all be synchronized with each other, and with the measurements of the induced heat flows.

In step 1004, residual heat flow is determined from the determined induced thermal flows and by measuring a change in the internal and external environments. For example if the internal environment stays static (e.g., temperature, pressure, and humidity do not change), than the residual heat flow may be determined as $Q_{ENV}=Q_{HVAC}-Q_{EL}-Q_W-Q_G-Q_P$. In other embodiments, residual heat flow $Q_{ENV}$ may be determined by taking into consideration the induced heat flows combined with changes in the internal environment ($T_{ENVI}$, $P_I$, and $H_I$), changes in temperature of internal object 801, and/or changes in temperature of the structure of building envelope 800.

Based on the determined residual thermal flow $Q_{ENV}$, and the measured environments, the actual thermal performance of the building envelope may be determined in step 1005. The actual thermal performance can be calculated as a composite thermal resistance factor, $R_C$, which not only includes an $R_{VALUE}$ characterizing conduction, but also incorporates the other residual thermal paths discussed above due to radiation, convection, and infiltration. In various embodiments, measured $R_C$ may thus be a real-time function of the measured environmental variables. In other embodiments a single $R_C$ value may be determined from the measured parameters, as a value defined over an average period, and/or at predefined environmental conditions. In various embodiments, the measured $R_C$ function or single $R_C$ value may be specified in construction or sales contracts, as a design metric or contractual obligation to meet by one party to the contract.

In step 1006, an error may be quantified between the measured $R_C$ and a modeled $R_C$ based on a modeled design. In step 1007, a source of the error may be determined based on the type of error found. For example, if the quantified error indicates that thermal conduction was a primary factor in the error, than a builder may conclude that a wall was not assembled according to specification.

In step 1008, reports may be generated which detail the errors. The reports may be provided at the conclusion of construction of the building, periodically during operation of the building to stakeholders, such as owners, building managers, and leaseholders, or provided in real time through, for example, web applications and analytical engines, which may continually calculate and display $R_C$ which may vary based on changing conditions.

In various embodiments, process 1000 may be performed in a static manner, such that one or more of the induced thermal paths may be inhibited. While inhibited, step 1003 may be performed to determine residual heat flow by measuring over time, the inside environment and/or building envelope temperature approaching equilibrium with the outside environment. For example, electric, gas, and water utilities may be cut off from the building, and all ventilation from an HVAC system shut. Once induced heat flow is inhibited, various environmental conditions may be monitored over time, such as $T_{AIRI}$, $H_I$, $B_I$, $P_I$, $T_{ENVI}$, $T_{AIRO}$, $H_O$, $B_O$, $P_O$, $T_{ENVO}$, $W_O$, Time, Date, temperature of the envelope, temperature of inside objects, and/or temperature of outside objects. Where no thermal paths are induced, any heat transfer is typically residual. $R_C$ may then be determined as a function of time during which the two environments approach equilibrium with each other. In one embodiment, the observation of the measured environment may occur over a limited specific interval after the induced heat paths have been shut off. The change in temperature between the inside and outside temperatures over the fixed interval may be specified as the thermal resistance factor, $R_C$. Alternatively, the maximum amount of time for the inside environment to reach equilibrium with the outside environment may be measured within a predetermined threshold. The maximum amount of time to reach equilibrium under the specific conditions may be specified as the thermal resistance factor, $R_C$. In either case, specific initial outside and inside temperatures or other environment variables may be specified.

In other various embodiments, process 1000 may be performed in a dynamic manner, where changes in the induced thermal paths are measured and tracked over time. For example, heat flow from occupants may be tracked in real time so that $R_C$ may be determined under conditions in which the building is often used. In another example, heat flow in a hotel may be tracked in which occupants, electricity, gas, and water are monitored. Determining heat flow through process 1000 may show that excessive heat from shower and/or laundry waste water is being lost from the building envelope. In this sense, process 1000 may be used not only as an audit of the residual thermal performance of the building envelope, but also as an audit of unintended induced heat paths such as drain water. Process 1000, in one embodiment may thus be used to determine how both residual and induced heat paths may be improved.

In both static and dynamic embodiments, process 1000 may be repeated continuously at periodic intervals (e.g., weeks, days, years, months, etc.) through loop 1011 in order to track changes in the thermal performance of a building envelope over time. Changes may be the result of aging of materials, defects in materials, modifications to building structures and systems, or damage to the structures. Changes may also result from changes in the environment (e.g., seasonal changes, solar cycles), or may result from changes in the building envelop and adjacent structures (e.g., new adjacent buildings, changes in occupancy, remodeling, etc.).

In both static and dynamic embodiments, process 1000 may also be applied at different stages of construction of the building envelope. For example, process 1000 may be performed when the outer layer (e.g., brick, concrete) has been completed, but interior build out has not yet been completed. In this way, thermal performance (e.g., thermal resistance and thermal mass) may be evaluated for different components and layers of the building envelope.

In either the static and dynamic embodiments for determining $R_C$, thermal mass of $M_{ENV}$ and $M_I$ may also be determined in step 1009 by monitoring the rise in temperature of building envelope 800 and object 801, and by monitoring any delay in the conductance of heat through from the inside environment and outside environment. For example, using the methods discussed above, induced and residual heat flow may be measured over a fixed period of time and integrated to determine the total amount of heat energy flowing into and out of the building envelope. A composite thermal mass of the building structure, $M_{ENV}$ or $M_I$ (or a composite of the two) may be determined as the difference between the heat flow in and out of the building per degree temperature change of the building structure over the measuring period. We note here that $M_{ENV}$ or $M_I$, may not be thermal mass in strict definition of the term since the temperature of the building structure may vary from location to location within the building envelope. Accordingly, in various embodiments, we use a thermal mass factor $M_C$, which may be based on estimates or averages of heat flow and temperature changes. In one example, $M_C$ may be defined in terms of energy storage of the building envelope with respect to a change in the inside environment temperature (i.e., $\Delta T_{AIRI}$) at equilibrium, given otherwise static environmental conditions.

We have simplified the calculation of the thermal mass $M_{ENV}$, and thermal mass factor $M_C$, however in some embodiments a more complicated measure the building ability to store energy. For example, heat flow $Q_W$ may be more efficiently transferred to the thermal mass $M_{ENV}$ than heat flow $Q_G$. Therefore, in certain embodiments, the thermal mass $M_{ENV}$, and thermal mass factor $M_C$ may be employed which is based on the building envelope's energy storage properties across different environmental conditions, with the different types of heat flows.

The determined thermal resistance factor $R_C$ and thermal mass factor $M_C$ may be applied in various applications in step 1010. In the various applications of step 1010, a one-time measurement of $R_C$ and/or $M_C$, a periodically/continuously measured $R_C$ and/or $M_C$, and/or measured changes in $R_C$ and/or $M_C$ over time may be applied. In one illustrative application, the method of measuring $R_C$ and/or $M_C$ and a specific measured $R_C$ and/or $M_C$ may be specified in construction or sales contracts as a performance metric. Specific damages may further be specified in the contracts based on $R_C$ and/or $M_C$. For example, the contract may specify how to calculate a monetary loss in heating or cooling a building based on the delta between a specified $R_C$ and/or $M_C$ in the contract and a measured $R_C$ and/or $M_C$. In some variations, specified, forecast, or measured environmental variables may further be considered in determining the monetary loss. In another illustrative application, the specific methods for determining $R_C$ and/or $M_C$ may be used as industry standards to compare different structures, or to establish minimum build criteria.

In another variation, resistance factors $R_C$ and thermal mass factors $M_C$ may be collected from a number of buildings may be posted on a website or provided in a publication for providing comparative performance data between buildings. The data may provide $R_C$ and/or $M_C$ or some performance metric derived from these factors, and may organize the data in a manner to rank the building in order of performance. The builders of the buildings may be ranked in a similar manner based on the buildings they construct. The builder's performance may be based on one building or a number of building the builder has constructed. In this manner, historical $R_C$ and $M_C$ data may be used for certification purposes of different builders.

In another illustrative embodiment of step 1010, $R_C$ and/or $M_C$ may be periodically tracked in real-time and used in a closed loop system for autonomously controlling a climate control system (e.g., HVAC) of the building. The periodically tracked $R_C$ and/or $M_C$ may be used in conjunction with measured or forecasted environment conditions, and/or in conjunction with varying cost rates of energy source to control the climate control system. For example, on a night during off-peak rates for electricity, when cold whether is forecast for the next day, the inside environment may be pre-heated such that energy is stored in the thermal masses of the inside object 801 and the building envelope 800 for later dissipation into the inside environment during the day when the building is being occupied and when electricity is at its peak rate. In this example, the determined $R_C$ and $M_C$ may be used to determine the amount, duration, and time to pre-heat the building in order to optimize cost savings. Because $R_C$ and $M_C$, energy rates, and thermal mass inside the building envelope may change over time, the optimum parameters for pre-heating may change as well. $R_C$ and/or $M_C$ may be applied to pre-cooling as well. The determined $R_C$ and/or $M_C$ may show that no cost savings could be achieved because the thermal insulation of the building envelope is insufficient to retain heat for a required amount of time.

In various aspects, dynamically determining $R_C$ and $M_C$ may provide a means for managing use of the building. For example, $R_C$ and/or $M_C$ may be determined on a room by room basis, and show that some areas of the building are inefficient to heat or cool. Building use may be adapted such the spaces with poor $R_C$ and $M_C$ may be used for storage or other purpose where climate control is less important.

Referring to FIG. 1, to perform the steps of process 1000, the induced heat paths may be monitored. Using the electrical heat path as an example, distribution systems may be designed to support specific users, and/or specific tenants of the facility. The design of the distribution system may provide individual tenants and individual employees of the tenant their own supply feed, distribution service, and/or different combinations thereof such that use and/or generation of an energy source by the individual tenant/employee may be uniquely measured using a meter on the tenant's/employee's supply feed or using a sub-meter on the tenant's distribution service. In various aspects, such monitoring of individual tenants or portions of the facility may be used to determine induced heat flow for building envelopes enclosing only a portion within the overall building. In various embodiments, induced heat flow may be monitored on a per tenant basis. For example one tenant may have several more occupants (e.g., self contained heat emitting bodies), and thus induce greater heat flow. Lease rates may be proportioned between tenants based on the relative induced heat flows.

In various embodiments, meter 104, sub-meter 105, and light/load meter 133, may be added to a supply feed, distribution service, or particular load respectively, to measure and record supply and consumption of the energy source over time. From these measurements, analysis may be performed according to certain embodiments to determine the induced heat flow for the building envelope of the entire building or for a smaller volume within the overall building.

Meter 104, sub-meter 105, and sensor 133 may be variously configured. In one embodiment, meters 104, 105, and 133 may include one or more sensors. Various sensors appropriate for measuring the consumption and/or supply of the energy source will differ depending on the energy source being measured. As previously discussed, in the electrical distribution system in system 100, the sensor may be an inductively coupled transformer, a current shunt, or other appropriate sensor for measuring power, electrical current and/or voltage. In other distribution systems for other energy sources such as natural gas and water, appropriate flow meters may be used. For people or automobiles, thermal sensors, thermal imaging systems, imagers, etc. may be used. While meters 104, 105, and 133 are described with respect to electrical power, the various embodiments including the collection and processing of data will be the same regardless of the energy source.

As previously described with respect to meters 104 and 105, sensor 133 may further include a computing platform to operate the sensor, and accumulate pulse inputs (periodic measurements) from the meters and sensors. Meter 133 may include several sensors and accumulate data from several different paths in the distribution system. As an example, meter 133 may include a circuit board with 10 sensor channels for sensors which may each collect pulse data in parallel. A processor on the circuit board may read each channel and accumulate data in the same and/or separate memory devices (e.g. registers) for each channel. The meter 133 may further have a data display which scrolls periodically and/or continuously to illustrate the pulses per channel. In addition to the data display, meter 133 may have buttons or other inputs, which can be used for on-site programming and/or trouble shooting. After on-site programming/trouble shooting, further programming may be from a remote location and/or computer.

In various aspects, sensor 133 may transmit data to a server/workstation or other computing device as previously described with respect to meters 104 and 105. Once collected, the server/workstation may compile the data from each sensor/channel into time sequences of data. The detailed data sequences and graphs associated with individual meters may help pinpoint particular induced thermal paths.

Figure 11:
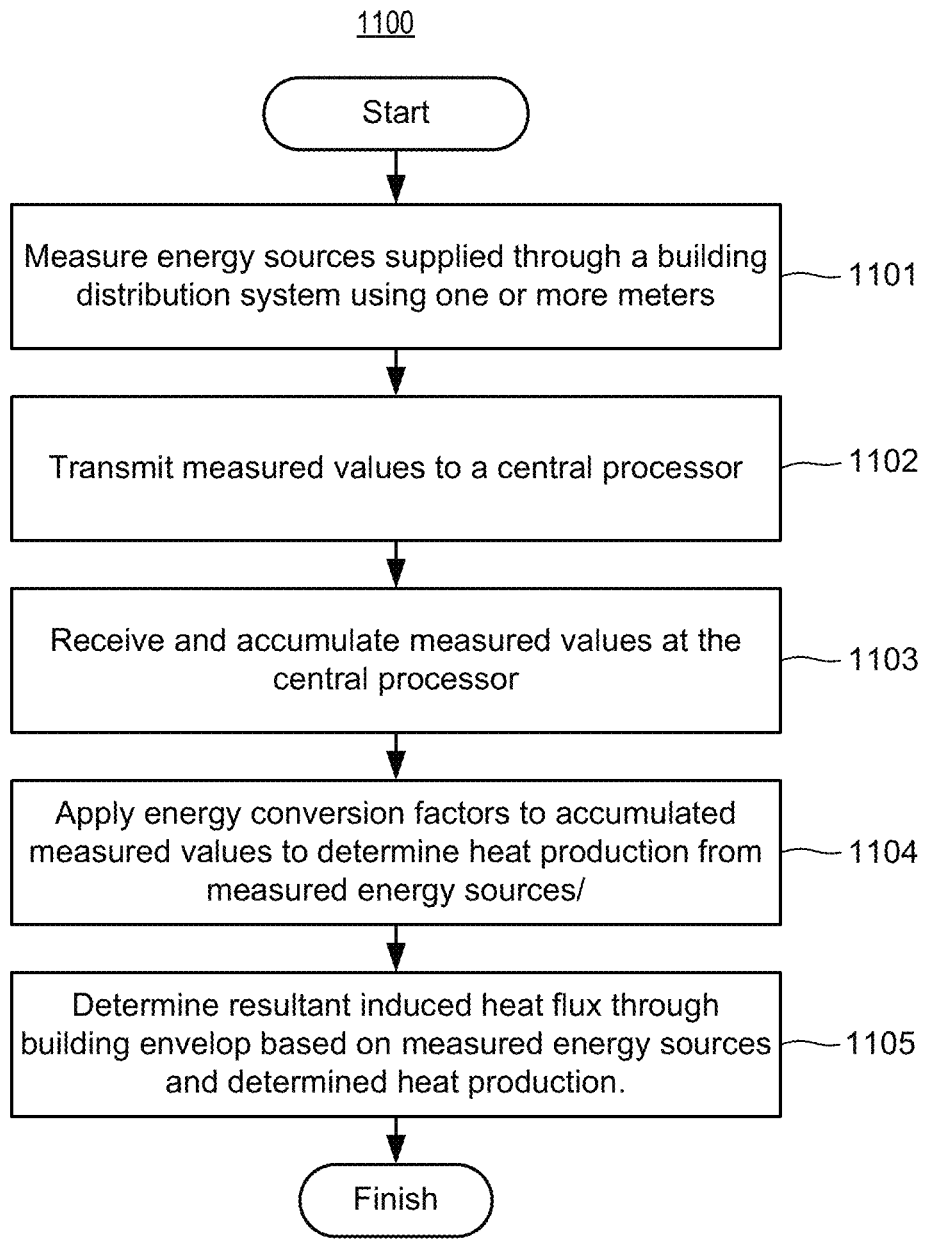
FIG. 11 illustrates a flow diagram of an embodiment for analyzing data sequences to determine induced heat flow from various energy sources.

FIG. 11 illustrates a process, according to some embodiments, to analyze data sequences to determine induced heat flow from various energy sources. Process 1100 starts at 1101 where the supply of an energy source is measured in a distribution system by a meter (e.g. 104). The measured values may then be transmitted from the meter in step 1102, and subsequently received by a processor (e.g. server/workstation 127) in step 1103. Steps 1101, 1102, and 1103 may be accomplished as already described with respect to FIG. 1 and may result in one or more data sequences. Steps 1101, 1102, and 1103 may occur on a pre-determined scheduled basis, as a result of the processor requesting the measured data from the meters, or both. In step 1104, conversion factors of the energy supply to heat production are retrieved from a database. Each conversion factor is a characterization of a loads production of heat from consumption of the energy source. In step 1105, the processor uses the conversion factors and the measured data sequences to determine the induced heat flow through the building envelope. These values may then be used in step 1002 of process 1000.

Figure 12:
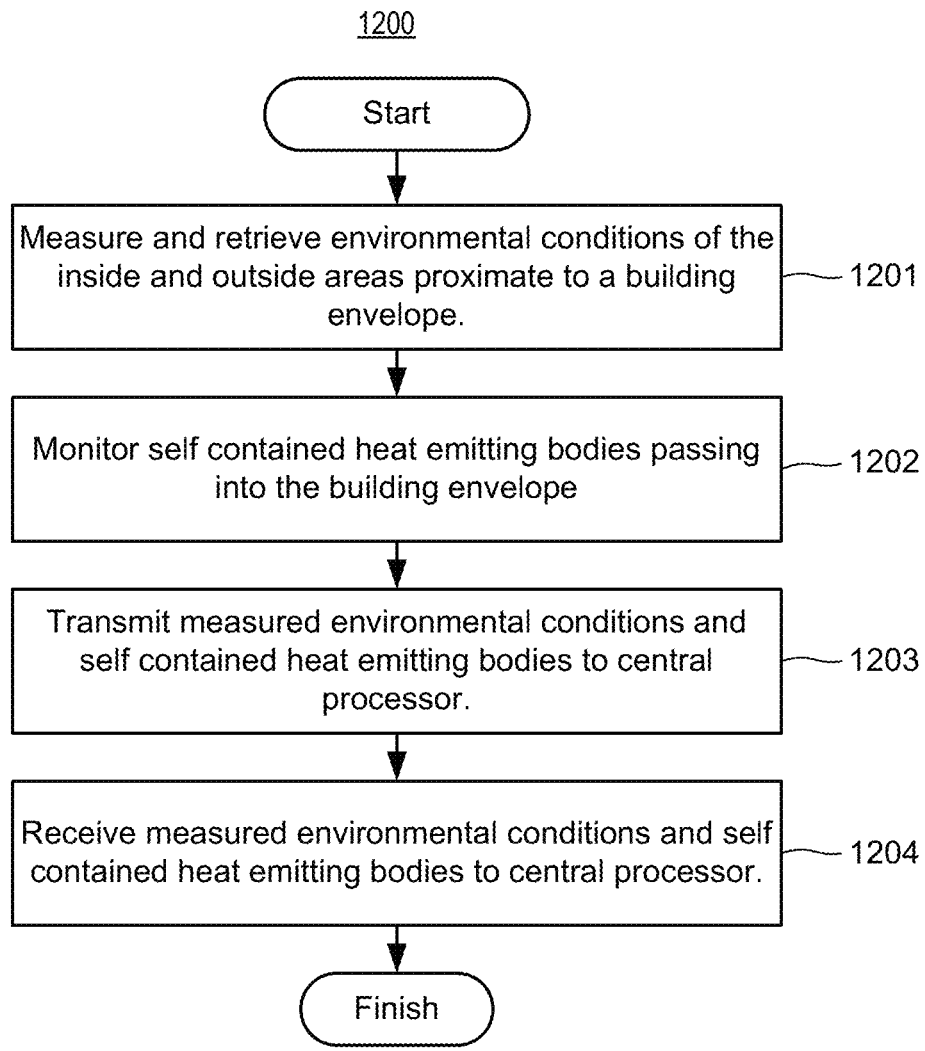
FIG. 12 illustrates a flow diagram of an embodiment for measuring environmental conditions and self contained heat emitting bodies.
Figure 13:
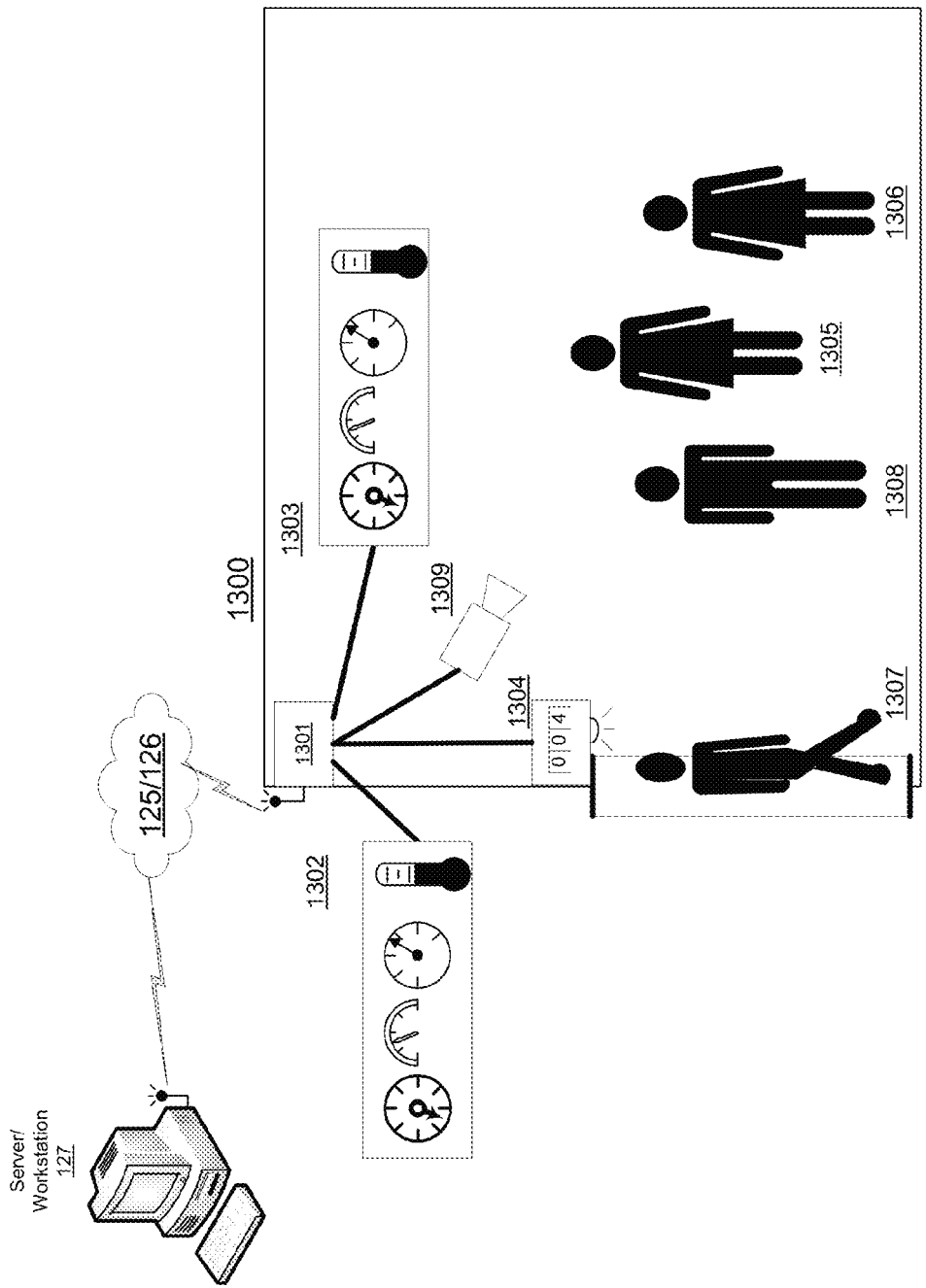
FIG. 13 illustrates an illustrative facility incorporating various sensors which may be used with various embodiments.

Process 1100 may be augmented with additional steps of process 1200 illustrated in FIG. 12, and described with respect to FIG. 13, for measuring environmental conditions and self-contained heat emitting bodies. In this illustrative embodiment, process 1200 starts at 1201 by measuring the environmental conditions illustrated in FIG. 9. For example, as illustrated in FIG. 13, instruments 1303 may be used to measure inside environmental conditions such as such as $T_{ENVI}$, $P_I$, and $H_I$, and instruments 1302 may be used to measure outside environmental conditions such as $T_{AIRO}$, $H_O$, $B_O$, $P_O$, $T_{ENVO}$, and $W_O$. Step 1201 may also include acquiring environmental conditions, weather forecasts and/or other data such as heating and cooling degree day forecasts and utility rate data from external sources such as web servers which compile and distribute such data.

Other operating conditions such as the presence or heat emission of a self contained heat emitting body may be monitored in step 1202. In step 1202, self contained heat emitting bodies 1305 to 1308 within room 1300 may be counted by a sensor 1304. Alternatively, heat signatures of the heat emitting bodies may be detected using thermal imaging device 1309. These sensors may monitor self contained heat emitting bodies as they enter and leave the building, and/or as they move from room to room within the building. FIG. 13 illustrates the heat emitting bodies as people, but the bodies could equally be another animal, an automobile, and/or other object that emits heat generated from internally stored energy.

In various embodiments, instruments 1302 and 1303 may include installed wired and/or wireless temperature transmitters (Infrared, RTD, thermistors, or any temperature measurement platform) on the inside, outside and within the building structure forming the building envelope. These sensors may be arranged in a matrix format and/or may be arranged to measure temperatures at particular points of interest. FIG. 9 details illustrative aspects of temperature instruments within 1302 and 1303.

In FIG. 14, wall 1400 is illustrated with four layers 1401-1405. As previously described, wall 1400 may include an outside concrete layer 1401, next to a thin air layer 1402, followed by a sheathing layer 1403, an insulation layer 1404, and a drywall layer 1405. In various embodiments represented by temperature instrument 1406, temperature sensors may be placed between each material layer making up a wall or enclosure. Temperature instrument 1406 may for example consist of six temperature sensors with each sensor embedded between each of layer as shown (dotted bubble provided for clarity). The sensors are coupled by wires or wireless transmitters through the layers to a measurement device 1407, which may be located on either side of the wall. With temperature instrument 1406 temperature may be detected at multiple depths in the wall simultaneously, periodically, and in real-time. Instrument 1407 may measure temperature data from the sensors periodically and relay the data as discussed with respect to FIGS. 4 and 12.

The sensors of temperature sensor 1406 may be installed during installation of the material layers, or the sensors may be installed by the material manufacture as an integral part of the material layers. For example, in one embodiment a manufacture of rolled fiberglass insulation, may imbed a string of wired sensors spaced and taped along the paper backing of the insulation roll.

In another illustrative embodiment of a temperature instrument, a temperature detection probe 1408 having the ability to measure temperature along incremental distances of the probe is inserted through the multiple layers of the wall. The probe may be a thin cylindrical (or other shape) rod which is inserted into a hole drilled or built into the wall. With the probe, temperature may be detected at multiple depths in the wall simultaneously, periodically, and in real-time. Instrument 1407 may measure or receive temperature data from probe 1408 via wired or wireless connection and periodically relay the data as discussed with respect to FIGS. 4 and 12.

Using the illustrative temperature instruments 1406, 1408, or other similar instrument, a gradient of temperature can thus be detected through the wall, and a more detailed view of the wall's thermal resistance ($R_{VALUE}$), thermal mass (M), thermal resistance factor ($R_C$), and thermal mass factor ($M_C$) can be determined.

In other aspects, instruments 1302 and 1303 may be used during the construction of the building envelope to determine the wall's thermal resistance ($R_{VALUE}$), thermal mass (M), thermal resistance factor ($R_C$) and thermal mass factor ($M_C$). For example, a thermal imaging camera may be used during the construction of a wall. As each layer of a wall is assembled, the thermal surface temperatures of the wall may be measured using the thermal imaging camera, or other thermal sensor. In this way, the contribution of each layer to the walls thermal resistance, thermal mass, or the thermal resistance factor may be independently verified. This may provide an advantage, for example, in detecting faulty or incorrectly installed material before the entire wall is assembled. As a further advantage of measuring each layers contribution, either before or during the completion of the wall, these embodiments are able to pinpoint the cause or causes of under or over thermal performance by a particular component of the construction.

The measurements obtained in process 1200 may be accompanied by meta-data such as time stamps or time intervals such that the operating conditions may later be correlated to data captured in processes 1000 and 1100. In step 1203, the measured environmental and other captured operating conditions are transmitted to the processor. FIG. 13 illustrates an exemplary data collection node 1301 collecting the measured values and transmitting them to the processor in server/workstation 127 through network 125/126, which may be the same as the communication paths describe with respect to FIG. 1, or which may different than, but of the same types as those of FIG. 1. Data collection node 1301, may be the same as meters 104, 105, and 133, or may be some other computing platform operating in the same manner as 104, 105, and 133 over the same types of communication links to transfer data to server/workstation 127. Server workstation 127 may be remotely located, or may be located within the building envelope. In step 1204, the processor in server/workstation 127 receives the transmitted data. The data may then be used in steps 1003 and 1004 of process 1000.

Returning to FIG. 14, plot 1409 illustrates the output of temperature sensors measured over time. Each of the plot line 1410-1415 represents temperature measured by the sensors on each surface of layers 1401-1405. The distance between each plot line represents the temperature difference through a layer. As is shown, the temperature difference through each layer may vary over time at different rates and magnitudes than other adjacent layers, depending on that layers thermal resistance and thermal mass. Using the plots, the thermal resistance and thermal mass may be determined from the plots in the same manner as previously discussed with respect to a single object.

Processes 1000, 1100, and 1200 may be performed by an autonomous processor that works continuously collecting data (e.g., pulse data), and determining $R_C$ and induced and residual heat flow in real-time or near real-time, and generating reports on a fixed schedule (i.e. daily). These reports may be generated in the form of hard-copies and mailed, in electronic form and sent via electronic mail, text message or other form of electronic transfer, or in the form of voice messages sent via a phone line. Further embodiments may allow the reports, including billing information and graphical data to be displayed on any customer interface device, desktop, laptop, PDA, Blackberry and or client internet portal, and may be further provided through a website hosted by the processor. By serving the data from a website, an interested party may be able to view usage and cost data and graphic displays in real-time and/or near real-time. As referred herein, "real-time" refers to updating the usage data as it is collected and calculated with little and/or relatively little delay other than the time it takes to process and/or transmit the data. The amount of delay may be a designed limit on processing time, such that the data may be used in closed loop control such as for use in controlling a climate control system. The delay may also simply be dependent on the resources available in measuring, transferring, and processing the data. For the purposes of this application, "real-time" and "near real-time" refers to the same concept in processing data.

Figure 7:
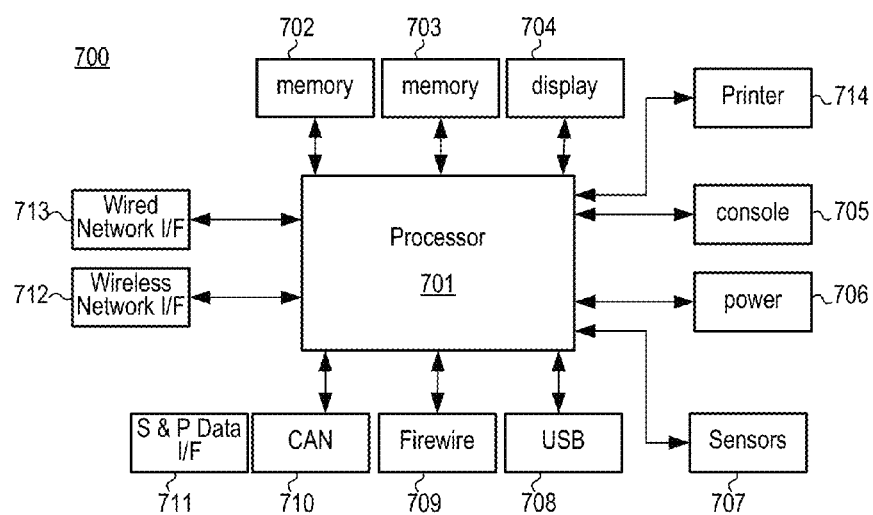
FIG. 7 illustrates a hardware block diagram of a processor according to some embodiments.

FIG. 7 is a block diagram of an exemplary computing platform 700 of various embodiments, including an autonomous processor, meters, sub-meters, communication devices, and other equipment for performing the various described processes. The various embodiments may be implemented as one computing platform or multiple computing platforms, operating independently, or in a coordinated manner, such as in a computer cluster. Using multiple computing platforms may provide redundancy, increased analysis and/or data storage, expanded capability to operate more users and/or geographically disperse users and consumable products, and other advantages.

A processor 701 is configured to perform the various operations of system control, telemetry sensing and gathering, data reception and transmission, sensor calibration and control, consumable product source and load control, telemetry processing. Processor 701 may implement the various algorithms and processes as described herein, including determining heat flow, thermal resistance factors, and thermal mass factors, producing secondary data products such as usage determinations and reports, determining signatures of users and occupants, and determining specific user access to consumable products/energy sources. The algorithms implemented by processor 701 may include pattern matching algorithms, signal processing algorithms, and artificial intelligence algorithms such as neural networks. Processor 701 may further control the operation of other components of computing platform 700 or may control other remote equipment. Processor 701 may include one or more microprocessors, application specific integrated circuits, field programmable gate arrays, programmable interconnect and combinations thereof. Processor 701 may be configured to communicate with and controls the various components within 700 over one or more buses.

In at least some embodiments, processor 701 carries out operations described herein according to machine readable instructions (e.g. software, firmware, hardware configuration files, etc.) stored in memory 702 and/or 703 and/or stored as hardwired logic gates within processor 701. Memory 702 and 703 may further store one or more databases which may be used to store energy conversion factors, occupant heat signatures, consumption signatures of various consumable product users, sensor telemetry, calibration information, control information for various sensors, actuators, and other system components, costing information of various energy sources/consumable products, environmental information, facility information, and other operating conditions. The various databases may permit access by one or more processors in 701 or one or more other processing platforms 700. The various databases may be organized to include meta-data for the various contents to enable selective retrieval of data to enable the processing as described herein. As one example meta-data may be added to consumption data such that it is retrievable from the database in the correct time order, or such that signatures and data specific to certain tenants or areas of the building are provided from the database as a group of data that is easily combinable.

Memory 702 and 703 may include volatile and non-volatile memory and may include any of various types of storage technology, including one or more of the following types of storage devices: read only memory (ROM) modules, random access memory (RAM) modules, magnetic tape, magnetic discs (e.g., a fixed hard disk drive or a removable floppy disk), optical disk (e.g., a CD-ROM disc, a CD-RW disc, a DVD disc), flash memory, and EEPROM memory.

Main processor 701 may be configured to communicate with other computing systems, meters, sub-meters, etc. through various interfaces such as wireless interfaces that may include additional hardware and/or firmware. Such interfaces may include one or more USB interfaces 708, Firewire interfaces 709, CAN protocol or other standard sensor interfaces 710, other serial or parallel data interfaces 711, and/or one or more wired and/or wireless network interfaces 712, 713. For example, communication to remote hardware may be accomplished through public and/or private networks using network interfaces such as wireless interfaces 712, wired interfaces 713, combinations of such interfaces and other equipment. For example, wireless interface 712 may be a local WiFi interface connected through a modem of a land line DSL, Coax, or Fiber-optic service provider network which connects to the Internet. Alternatively, wireless interface 712 may be equipment for connecting to a satellite or a cellular network as commonly used for cell phones, pagers, security systems, and personal digital assistants (PDAs).

For human interaction with the system, computing platform 700 may include a display for presenting a graphical user interface, graphs, charts, configuration information, or other data relating to the embodiments described herein. Computing platform 700 may further include a console 705 for human interaction and control of the various embodiments, and a printer 714 or other output device for generating records such as invoices and usage reports. Such consoles may include keyboards, mice or other input output devices. The display, console, and printer may be co-located with the other components of 700, or may be remote from 700. For example, several of the components of 700 may operate as a server that is remotely accessed over the Internet or private network and which may provide web pages for presenting and interacting with the system.

Computing platform 700 may further include other equipment such as power supply 706, battery backups, fuses or other circuit protection features, finger print readers and other security devices, expansion slots for additional hardware, audio equipment, infrared ports, etc.

The foregoing description is not intended to be exhaustive or to limit embodiments of the present invention to the precise form disclosed, and modifications and variations are possible in light of the above teachings or may be acquired from practice of various embodiments. The embodiments discussed herein were chosen and described in order to explain the principles and the nature of various embodiments and their practical application to enable one skilled in the art to utilize the present invention in various embodiments and with various modifications as are suited to the particular use contemplated. The features of the embodiments described herein may be combined in all possible combinations of methods, apparatuses, modules, systems, and machine-readable storage memory. Any and all permutations of features from the above-described embodiments are within the scope of the invention. For example, in performing processes 300, 400, 600, 1000, 1100, and 1200, the various computing platforms performing the processes may perform the various steps in a different order, may combine certain steps from the different processes, or may omit certain steps.

Further, the various embodiments have been described in the context of public utilities such as electricity and gas, and in the context of human occupation. Such embodiments are exemplary only and the principles described herein are equally applicable to other energy sources where the distribution to multiple buildings may be measured and analyzed. Other example include distribution of compressed air, inert gases, steam, ice, dry ice, agricultural irrigation, livestock, domestic animals, geothermal, nuclear, biofuels, biomass, and any other energy source.

We claim:

1. A method performed by a consumable-product distribution system comprising:
    generating, by a meter, a time-sequence of data by measuring over a time-interval a series of loads;
    measuring, with a meter of a consumable-product distribution system, a value of a consumable product supplied through the consumable-product distribution system to a facility, wherein the measured value comprises a second time-sequence of data of the facility's access to the consumable product, and wherein the consumable-product distribution system connects a plurality of loads in the facility to the consumable product;
    transmitting, by the meter of the consumable-product distribution system to a processor of the consumable-product distribution system, the measured value of the consumable product supplied through the consumable-product distribution system to the facility;
    retrieving, by the processor of the consumable-product distribution system, a plurality of load signatures from a database of the consumable-product distribution system, each load signature comprising a time-sequence of data of a corresponding load's access to the consumable product;
    comparing, by a-the processor of the consumable-product distribution system, the time-sequence of data of each of the plurality of load signatures to the second time-sequence of data of the measured value; and
    determining, by the processor of the consumable-product distribution system, an amount of the consumable product accessed by a first load of the plurality of loads based on the comparing.

2. The method of claim 1, wherein the processor of the consumable-product distribution system determines the amount of the consumable product accessed by the first load using an artificial intelligence process.

3. The method of claim 1 further comprising:
    generating, by the processor of the consumable-product distribution system, a customized report of the access to the consumable product by the first load over a fixed duration.

4. The method of claim 1 further comprising:
determining, by the processor of the consumable-product distribution system, a cost for the access to the consumable product by the first load over a fixed duration; and
generating, by the processor of the consumable-product distribution system, a report including the cost.

5. The method of claim 4, wherein the consumable product is a public electrical power utility and the cost is based on tiered utility rates over the fixed duration.

6. The method of claim 1, wherein the consumable product is electrical power and the plurality of loads are electrical loads.

7. The method of claim 1, wherein the consumable product is a public utility.

8. The method of claim 1, wherein the plurality of loads include at least one of HVAC components and facility lighting.

9. The method of claim 1 further comprising:
receiving, by the processor of the consumable-product distribution system, an operating condition of the first load, wherein the determining, by the processor of the consumable-product distribution system, the amount of the consumable product accessed by the first load is further based on the operating condition.

10. The method of claim 9 further comprising:
retrieving, by the processor of the consumable-product distribution system, the operating condition from the database.

11. The method of claim 9 further comprising:
receiving, by the processor of the consumable-product distribution system, the operating condition as a second measured value from the facility.

12. The method of claim 9, wherein the operating condition includes, for a portion of the facility, one of a load factor, an area square footage, and an insulation factor.

13. The method of claim 9, wherein the operating condition includes a measured count of persons within a portion of the facility.

14. The method of claim 13 further comprising:
autonomously counting, by a sensor of the consumable-product distribution system, the persons within the portion of the facility;
generating, by the sensor of the consumable-product distribution system, the measured count; and
transmitting, by the sensor of the consumable-product distribution system, the measured count to the processor.

15. The method of claim 13, wherein the operating condition further includes a time interval of when the persons are in the portion of the facility.

16. The method of claim 9, wherein the operating condition includes a temperature outside of the facility.

17. The method of claim 1 further comprising:
requesting, by the processor of the consumable-product distribution system, the measured value from the meter of the consumable-product distribution system at the facility, wherein the processor of the consumable-product distribution system is located remotely from the facility.

18. The method of claim 1, wherein the measured value is transmitted by the meter of the consumable-product distribution system to the processor of the consumable-product distribution system through a wireless communication network.

19. The method of claim 1, wherein the amount of the consumable product accessed by the first load is a negative quantity representing an amount of the consumable product produced by the first load.

20. The method of claim 1, wherein the determining the amount of the consumable product accessed by the first load of the plurality of loads based on the comparing comprises determining the amount of the consumable product accessed by the first load in real time.

* * * * *